United States Patent
Morre et al.

(10) Patent No.: US 9,804,166 B2
(45) Date of Patent: *Oct. 31, 2017

(54) METHODS FOR SINGLE CHAIN VARIABLE REGION ENOX2 ANTIBODIES FOR CANCER DETECTION AND DIAGNOSIS

(71) Applicants: Mor-NuCo Enterprises, Inc., West Lafayette, IN (US); Nicholas J. Miner, Lafayette, IN (US)

(72) Inventors: D. James Morre, West Lafayette, IN (US); Brandon Eugene Hostetler, West Lafayette, IN (US); James Jinpal Kim, West Lafayette, IN (US)

(73) Assignee: Mor-NuCo Enterprises, Inc., West Lafayette, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/205,656

(22) Filed: Jul. 8, 2016

(65) Prior Publication Data

US 2017/0030918 A1 Feb. 2, 2017

Related U.S. Application Data

(60) Division of application No. 14/229,091, filed on Mar. 28, 2014, now Pat. No. 9,459,256, which is a continuation of application No. PCT/US2012/059141, filed on Oct. 5, 2012.

(60) Provisional application No. 61/543,931, filed on Oct. 6, 2011.

(51) Int. Cl.

| | |
|---|---|
| *G01N 33/53* | (2006.01) |
| *G01N 33/574* | (2006.01) |
| *C07K 16/18* | (2006.01) |
| *C07K 16/40* | (2006.01) |
| *C07K 14/79* | (2006.01) |
| *C07K 14/81* | (2006.01) |
| *C12N 9/02* | (2006.01) |
| *C12N 9/16* | (2006.01) |
| *C12N 9/96* | (2006.01) |
| *G01N 27/447* | (2006.01) |

(52) U.S. Cl.
CPC ....... *G01N 33/57492* (2013.01); *C07K 14/79* (2013.01); *C07K 14/8125* (2013.01); *C07K 16/18* (2013.01); *C07K 16/40* (2013.01); *C12N 9/0036* (2013.01); *C12N 9/16* (2013.01); *C12N 9/96* (2013.01); *C12Y 106/00* (2013.01); *C12Y 301/03001* (2013.01); *G01N 27/4473* (2013.01); *G01N 27/44726* (2013.01); *G01N 27/44747* (2013.01); *G01N 27/44795* (2013.01); *G01N 33/57419* (2013.01); *G01N 33/57423* (2013.01); *G01N 33/57488* (2013.01); *C07K 2317/622* (2013.01); *C07K 2319/61* (2013.01); *G01N 2333/705* (2013.01); *G01N 2333/902* (2013.01); *G01N 2333/90209* (2013.01); *G01N 2333/916* (2013.01)

(58) Field of Classification Search
None
See application file for complete search history.

(56) References Cited

U.S. PATENT DOCUMENTS

| | | |
|---|---|---|
| 7,053,188 B2 | 5/2006 | Morre et al. |
| 9,283,257 B2 | 3/2016 | Morre |
| 9,459,256 B2 | 10/2016 | Morre |
| 2003/0207340 A1 | 11/2003 | Morre et al. |
| 2009/0042209 A1 | 2/2009 | Hostetler |
| 2014/0212896 A1 | 7/2014 | Morre et al. |

FOREIGN PATENT DOCUMENTS

| | | |
|---|---|---|
| WO | 2011109663 A1 | 9/2011 |
| WO | 2013052926 A2 | 4/2013 |

OTHER PUBLICATIONS

Bird, et al. "Single-chain antigen-binding proteins." Science, Oct. 21, 1988, vol. 242, No. 4877, pp. 423-426.
Bruno, et al., "Stimulation of NADH oxidase activity from rat liver plasma membranes by growth factors and hormones is decreased or absent with hepatoma plasma membranes" Biochemical Journal, Jun. 15, 1992, vol. 284, No. 3, pp. 625-628.
Cho, et al., "Monoclonal antibody to a cancer-specific and drug-responsive hydroquinone (NADH) oxidase from the sera of cancer patients." Cancer Immunology, Immunotherapy, May 2002, vol. 51, No. 3, pp. 121-129.
Chomczynski, et al. "Single-step method of RNA isolation by acid guanidinium thiocyanate-phenol-chloroform extraction." Analytical Biochemistry, Apr. 1987, vol. 162, No. 1, pp. 156-159.
Chueh, et al., "Molecular Cloning and Characterization of a Tumor-Associated, Growth-Related, and Time-Keeping Hydroquinone (NADH) Oxidase (tNOX) of the HeLa Cell Surface." Biochemistry, Jan. 11, 2002, vol. 41, No. 11, pp. 3732-374.
Daugherty, et al. "Polymerase chain reaction facilitates the cloning, CDRgrafting, and rapid expression of a murine monoclonal antibody directed against the CD18 component of leukocyte integrins." Nucleic Acids Research, Mar. 25, 1991, vol. 19, No. 9, pp. 2471-2476.

(Continued)

*Primary Examiner* — Jacob Cheu
(74) *Attorney, Agent, or Firm* — Edwin S. Flores; Chalker Flores, LLP

(57) ABSTRACT

Cancers of different cellular or tissue origins express different ENOX2 cancer isoforms or combinations of isoforms and shed these proteins into the circulation. Herein are disclosed methods both for cancer detection and diagnosis of particular origin, based on the patterns and molecular weights of the isoforms which allow the identification of the cell type and or tissue of origin of the neoplasm. Relative ENOX2 amounts are proportional to tumor burden and provide a reliable measure of response to therapy and disease progression. Also provided is the amino acid sequence to which the scFv antibodies bind as the molecular basis for the specificity of the test.

20 Claims, 6 Drawing Sheets

(56) References Cited

OTHER PUBLICATIONS

Davis, et al. "Single Chain Antibody (SCA) Encoding Genes: One-Step Construction and Expression in Eukaryotic Cells" (1991) Bio/Technology 9:165-169.
Davies, et al., "Spotlight on tNOX: A tumor-selective target for cancer therapies." Drug News Perspect, May 2006, vol. 19, No. 4, pp. 223-225.
Del Castillo-Olivares, et al., "A Drug-Responsive and Protease-Resistant Peripheral NADH Oxidase Complex from the Surface of HeLa S Cells." Archives of Biochemistry and Biophysics, Oct. 1, 1998, vol. 385, No. 1, pp. 125-140.
GenBank Accession No. AF207881, http://www.ncbi.nlm.nih.gov/nuccore/17149819, 2002 publication.
Glockshuber, et al. "A comparison of strategies to stabilize immunoglobulin Fv fragments." Biochemistry, Feb. 1990, vol. 29, No. 6, pp. 1362-1367.
Goncalves, et al., "Clinical Application of Proteomics in Breast Cancer: State of the Art and Perspectives." Medical Principles and Practice, vol. 20, No. 1, 2011, pp. 4-18.
Gough, NM "Rapid and quantitative preparation of cytoplasmic RNA from small numbers of cells." Analytical Biochemistry, Aug. 15, 1988, vol. 173, No. 1, pp. 93-95.
Hostetler, et al. "Cancer Site-Specific Isoforms of ENOX2 (tNOX), A Cancer-Specific Cell Surface Oxidase." Clinical Proteomics, Jul. 24, 2008, vol. 5, pp. 46-51.
Howlander, et al. SEER Cancer Statistics Review, 1975-2012, National Cancer Institute, Bethesda, Md, 2014 publication.
Huston, et al. "Protein Engineering of Antibody Binding Sites: Recovery of Specific Activity in an Anti-Digoxin Single-Chain Fv Analogue Produced in *Escherichia coli*." PNAS, Proceedings of the National Academy of Sciences, Aug. 1, 1988, vol. 85, pp. 5879-5883.
Jones, et al. "Rapid PCR-Cloning of Full-Length Mouse Immunoglobulin Variable Regions." Bio/Technology, Jan. 1991, vol. 9, pp. 88-89.
Korean Intellectual Property Office, International Search Report and Written Opinion for PCT/US2012/059141 dated Mar. 25, 2013, 14 pp.
Morre, "The antitumor sulfonylurea N-(4-methylphenylsulfony)-N'-(4-chlorophenyl) urea (LY181984) inhibits NADH oxidase activity of HeLa plasma membranes." Biochimica et Biophysica Acta, Nov. 22, 1995, vol. 1240, pp. 11-17.
Morre, et al., "Capsaicin inhibits preferentially the NADH oxidase and growth of transformed cells in culture." PNAS, Proceedings of the National Academy of Sciences, Mar. 14, 1995, vol. 92, No. 6, pp. 1831-1835.
Morre, et al., "NADH Oxidase Activity from Sera Altered by Capsaicin is Widely Distributed among Cancer Patients." Archives of Biochemistry and Biophysics, Jun. 15, 1997, vol. 342, No. 2, pp. 224-230.
Morre, et al. "A circulating form of NADH oxidase activity responsive to the antitumor sulfonylurea N-(4-methlyphenylsulfonyl)-N'-(4-chlorophenyl)urea (LY181984) specific to sera from cancer patients." Journal of Bioenergetics and Biomembranes, Mar. 4, 1997, vol. 29, No. 3, pp. 281-289.
Morre, D.J. NADH Oxidase: A Multifunctional Ecto-proteins of the Eukaryotic Cell Surface. In: Asard, H., Bérczi, A. and Caubergs, R., Eds., Plasma Membrane Redox Systems and Their Role in Biological Stress and Disease, Kluwer Academic Publishers, Dordrecht, 1998, pp. 121-156.
Morre, et al. "Surface NADH oxidase of HeLa cells lacks intrinsic membrane binding motifs." Archives of Biochemistry and Biophysics, Aug. 15, 2001, vol. 392, No. 2, pp. 251-256.
Morre, et al., "Cell surface NADH oxidases (ECTO-NOX proteins) with roles in cancer, cellular time-keeping, growth, aging and neurodegenerative disease." Free Radical Research, Aug. 2003, Vo. 37, No. 8, pp. 795-805.
Morre, et al., "Cancer Type-Specific tNOX Isoform: A Putative Family of Redox Protein Splice Variants with Cancer Diagnostics and Prognostic Potential" Biofactors, Aug. 26, 2009, vol. 34, No. 3, pp. 201-207.
Morre, et al., "Early Detection: An Opportunity for Cancer Prevention Through Early Intervention." Cancer Prevention—from Mechanisms to Translational Benefits, Apr. 20, 2012, pp. 389-402.
Tang, et al. "Alternative splicing as the basis for specific localization of tNOX, a unique hydroquinone (NADH) oxidase, to the cancer cell surface." Biochemistry, May 21, 2007, vol. 46, pp. 12337-12346.
Wang. et al., "NADH oxidase activity (NOX) and enlargement of HeLa cells oscillate with two different temperature-compensated period lengths of 22 and 24 minutes corresponding to different NOX forms." Biochimica et Biophysica Acta, Apr. 19, 2001, vol. 1539: pp. 192-204.
Wu, et al., "Next-Generation Sequencing of MicroRNAs for Breast Cancer Detection." Journal of Biomedicine and Biotechnology, Mar. 24, 2011, vol. 2011, pp. 597-145.
Braman, et al., "Site-Directed Mutagenesis Using Double-Stranded Plasmid DNA Templates," Chapter 3 of Methods in Molecular Biology, vol. 57, In Vitro Mutagenesis Protocols, 1996, pp. 31-44.
Jiang, Z., et al., "Molecular Cloning and Characterization of a Candidate Human Growth-Related and Time-Keeping Constitutive Cell Surface Hydroquinone (NADH) Oxidase," Biochemistry, vol. 47, No. 52, Sep. 2008, pp. 14028-14038.
Lee et al., "Effect of BRCA1/2 mutation on short-term and long-term breast cancer survival: a systematic review and meta-analysis." Breast Cancer Research and Treatment, Jul. 2010, vol. 122, Issue 1, pp. 11-25.
Morre, et al. (1988) "Inhibition of Plasma membrane redox activities and elongation of growth of soybean," Phsiologia Plantarum, vol. 72, 1988, pp. 236-240.
Morre, D.J., et al. (1999) "Use of dipyridyl-dithio substrates to measure directly the protein disulfide-thiol interchange activity of the auxin stimulated NADH: Protein disulfide reductase (NADH oxidase) of soybean plasma membranes," Molecular and Cellular Biochemistry, vol. 200, Dec. 15, 1998, pp. 7-13.
Morre, D.J., et al. (1999) "Glaucarubolone and Simalikalactone D, Respectively, Preferentially Inhibit Auxin-Induced and Constitutie Components of Plant Cell Enlargement and the Plasma Membrane NADH Oxidase," Int. J. Plant Sci., 160(2), pp. 291-297.
Morre, et al., "The Auxin-Stimulated ENOX and Auxin Stimulation of Plant Growth," Chapter 10 of Ecto-Nox Proteins: Growth, Cancer; Aging, Springer Science+Business Media New York 2013, pp. 313-342.
Morre, et al., "Cancer Diagnostic Applications of ENOX2 Proteins," Chapter 12 of Ecto-Nox Proteins: Growth, Cancer; Aging, Springer Science+Business Media New York 2013, pp. 419-434.
Smith, PK, et al., "Measurement of protein using bicinchoninic acid," Anal. Biochem., May 15, 1987, vol. 163:1: 279 (Abstract).
Tang, et al., "Molecular Cloning and characterization of human age-related NADH oxidase (arNOX) proteins as members of the TM9 suprefamily of transmembrane proteins," Advances in Biological Chemistry, Apr. 2013, vol. 3, pp. 187-197.
Weinberg, R., The Biology of Cancer, Chapter 11, "Multi-Step Tumorigenesis," 2007, pp. 399-462.
Extended European Search Report of 16180364.8 dated Nov. 11, 2016, 12 pp.
Hoopes, et al., "Staining Electrophoretic Gels for Laccase and Peroxidase Activity Using 1,8-Diaminonaphthalene," Analyt. Biochem., 293 (1), May 1, 2001, pp. 96-101.
Morre, et al., "ENOX2-based early detection (ONCOblot) of asbestos-induced malignant mesothelioma 4-10 years in advance of clinical symptoms," Clin. Proteomics, 13:2, Jan. 22, 2016; 8 pp.
Sock, J., et al., "Activity Staining of Blotted Enzymes by Reaction Coupling with Transfer Membrane-Immobilized Auxiliary Enzymes," Analyt. Biochem., 171 (2), Nov. 16, 1987, pp. 310-319.

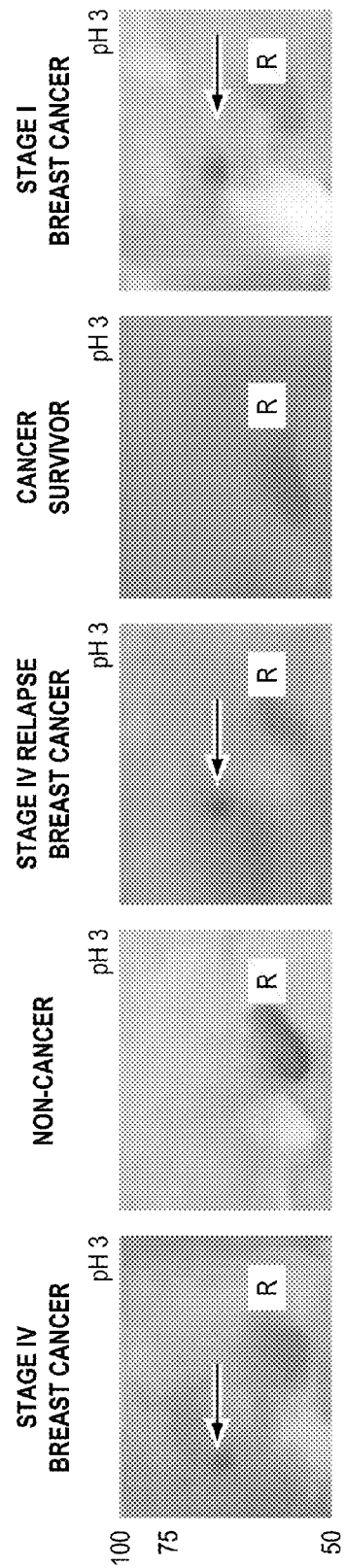

SEQUENCE LISTING

<160> NUMBER OF SEQ ID NOS: 20

<210> SEQ ID NO 1
<211> LENGTH: 357
<212> TYPE: DNA
<213> ORGANISM: Unknown
<220> FEATURE:
<223> OTHER INFORMATION: DNA of Heavy Chain ScFv (VH)

<400> SEQUENCE: 1

```
gaggtcaagc tgcaggagtc aggaactgaa gtggtaaagc ctggggcttc agtgaagttg      60
tcctgcaagg cttctggcta catcttcaca agttatgata tagactgggt gaggcagacg     120
cctgaacagg gacttgagtg gattggatgg attttcctg gagaggggag tactgaatac     180
aatgagaagt tcaagggcag ggccacactg agtgtagaca agtcctccag cacagcctat     240
atggagctca ctaggctgac atctgaggac tctgctgtct atttctgtgc tagaggggac     300
tactataggc gctactttga cttgtggggc caagggacca cggtcaccgt ctcctca        357
```

<210> SEQ ID NO 2
<211> LENGTH: 321
<212> TYPE: DNA
<213> ORGANISM: Unknown
<220> FEATURE:
<223> OTHER INFORMATION: DNA of Light Chain ScFv (VL)

<400> SEQUENCE: 2

```
gaaaatgtgc tcacccagtc tccagcaatc atgtctgcat ctccagggga gagggtcacc      60
atgacctgca gtgccagctc aagtatacgt tacatatatt ggtaccaaca gaagcctgga     120
tcctccccca gactcctgat ttatgacaca tccaacgtgg ctcctggagt cccttttcgc     180
ttcagtggca gtgggtctgg gacctcttat tctctcacaa tcaaccgaat ggaggctgag     240
gatgctgcca cttattactg ccaggagtgg agtggttatc cgtacacgtt cggagggggg     300
accaagctgg agctgaaagc g                                               321
```

<210> SEQ ID NO 3
<211> LENGTH: 738
<212> TYPE: DNA
<213> ORGANISM: Unknown
<220> FEATURE:
<223> OTHER INFORMATION: heavy chain of DNA of ScFv

<400> SEQUENCE: 3

```
gtggtaaagc ctggggcttc gaggtcaagc tgcaggagtc aggaactgaa catcttcaca      60
agttatgata gtgaagttg tcctgcaagg cttctggcta gacttgagtg gattggatgg     120
tagactgggt gaggcagacg cctgaacagg aatgagaagt tcaagggcag ggccacactg     180
agtgtagaca agtcctccag cacagcctat atggagctca ctaggctgac atctgaggac     240
tctgctgtct atttctgtgc tagaggggac tactataggc gctactttga cttgtggggc     300
caagggacca cggtcaccgt ctcctcagga ggcggtggat cggcggtgg cggctcgggt     360 ggcggcggct ctgaaaatgt gctcacccag tctccagcaa tcatgtctgc atctccaggg    420
```

```
gagagggtca ccatgacctg cagtgccagc tcaagtatac gttacatata ttggtaccaa    480
cagaagcctg atcctcccc cagactcctg atttatgaca catccaacgt ggctcctgga    540
gtcccttttc gcttcagtgg cagtgggtct gggacctctt attctctcac aatcaaccga    600
atggaggctg aggatgctgc cacttattac tgccaggagt ggagtggtta ccgtacacg    660 ttcggagggg ggaccaagct ggagctgaaa gcgaaagaaa ccgctgctgc taaattcgaa    720
cgccagcaca tggacagc                                                  738
```

<210> SEQ ID NO 4
<211> LENGTH: 256
<212> TYPE: PRT
<213> ORGANISM: Unknown
<220> FEATURE:
<223> OTHER INFORMATION: Light chain DNA of ScFv

<400> SEQUENCE: 4

Glu Val Lys Leu Gln Glu Ser Gly Thr Glu Val Val Lys Pro Gly Ala
1               5                   10                  15

Ser Val Lys Leu Ser Cys Lys Ala Ser Gly Tyr Ile Phe Thr Ser Tyr
            20                  25                  30

Asp Ile Asp Trp Val Arg Gln Thr Pro Glu Gln Gly Leu Glu Trp Ile
        35                  40                  45

Gly Trp Ile Phe Pro Gly Glu Gly Ser Thr Glu Tyr Asn Glu Lys Phe
    50                  55                  60

Lys Gly Arg Ala Thr Leu Ser Val Asp Lys Ser Ser Ser Thr Ala Tyr
65                  70                  75                  80

Met Glu Leu Thr Arg Leu Thr Ser Glu Asp Ser Ala Val Tyr Phe Cys
                85                  90                  95

Ala Arg Gly Asp Tyr Tyr Arg Arg Tyr Phe Asp Leu Trp Gly Gln Gly
            100                 105                 110

Thr Thr Val Thr Val Ser Ser Gly Gly Gly Ser Gly Gly Gly Gly
        115                 120                 125

Ser Gly Gly Gly Gly Ser Glu Asn Val Leu Thr Gln Ser Pro Ala Ile
    130                 135                 140

Met Ser Ala Ser Pro Gly Glu Arg Val Thr Met Thr Cys Ser Ala Ser
145                 150                 155                 160

Ser Ser Ile Arg Tyr Ile Tyr Trp Tyr Gln Gln Lys Pro Gly Ser Ser
                165                 170                 175

Pro Arg Leu Leu Ile Tyr Asp Thr Ser Asn Val Ala Pro Gly Val Pro
            180                 185                 190

Phe Arg Phe Ser Gly Ser Gly Ser Gly Thr Ser Tyr Ser Leu Thr Ile
        195                 200                 205

Asn Arg Met Glu Ala Glu Asp Ala Ala Thr Tyr Tyr Cys Gln Glu Trp
    210                 215                 220

Ser Gly Tyr Pro Tyr Thr Phe Gly Gly Gly Thr Lys Leu Glu Leu Lys
225                 230                 235                 240

Ala Lys Glu Thr Ala Ala Ala Lys Phe Glu Arg Gln His Met Asp Ser
                245                 250                 255

<210> SEQ ID NO 5
<211> LENGTH: 15
<212> TYPE: PRT
<213> ORGANISM: Unknown
<220> FEATURE:
<223> OTHER INFORMATION: Peptide of linker

<400> SEQUENCE: 5

Gly Gly Gly Gly Ser Gly Gly Gly Gly Ser Gly Gly Gly Gly Ser
1               5                  10                 15

<210> SEQ ID NO 6
<211> LENGTH: 45
<212> TYPE: DNA
<213> ORGANISM: Unknown
<220> FEATURE:
<223> OTHER INFORMATION: DNA for linker encoding

<400> SEQUENCE: 6
ggaggcggtg atcgggcgg tggcggctcg ggtggcggcg gctct            45

<210> SEQ ID NO 7
<211> LENGTH: 45
<212> TYPE: DNA
<213> ORGANISM: Unknown
<220> FEATURE:
<223> OTHER INFORMATION: DNA of s-peptide

<400> SEQUENCE: 7
aaagaaaccg ctgctgctaa attcgaacgc cagcacatgg acagc            45

<210> SEQ ID NO 8
<211> LENGTH: 37
<212> TYPE: DNA
<213> ORGANISM: Artificial Sequence
<220> FEATURE:
<223> OTHER INFORMATION: Heavy chain forward primer

<400> SEQUENCE: 8
ggcccagccg gccgaggtca agctgcagga gtcagga                     37

<210> SEQ ID NO 9
<211> LENGTH: 33
<212> TYPE: DNA
<213> ORGANISM: Artificial Sequence
<220> FEATURE:
<223> OTHER INFORMATION: Heavy Chain reverse primer

<400> SEQUENCE: 9
ctcggaacct gaggagacgg tgaccgtggt ccc                         33

<210> SEQ ID NO 10
<211> LENGTH: 36
<212> TYPE: DNA
<213> ORGANISM: Artificial Sequence
<220> FEATURE:
<223> OTHER INFORMATION: Light Chain forward primer

<400> SEQUENCE: 10
tccaaagtcg acgaaaatgt gctcacccag tctcca                      36

<210> SEQ ID NO 11
<211> LENGTH: 33
<212> TYPE: DNA
<213> ORGANISM: Artificial Sequence
<220> FEATURE:
<223> OTHER INFORMATION: Light chain reverse primer

<400> SEQUENCE: 11
agcggccgct ttcagctcca gcttggtccc ccc                         33

<210> SEQ ID NO 12
<211> LENGTH: 21

```
<212> TYPE: DNA
<213> ORGANISM: Artificial Sequence
<220> FEATURE:
<223> OTHER INFORMATION: Primer for heavy chain and linker amplification
      forward primer

<400> SEQUENCE: 12
gtcaagctgc aggagtcagg a                                              21

<210> SEQ ID NO 13
<211> LENGTH: 66
<212> TYPE: DNA
<213> ORGANISM: Artificial Sequence
<220> FEATURE:
<223> OTHER INFORMATION: Primer for heavy chain and linker amplification
      reverse primer

<400> SEQUENCE: 13
agagccgccg ccacccgagc cgccaccgcc cgatccaccg cctcctgagg agacggtgac    60
cgtggt                                                               66

<210> SEQ ID NO 14
<211> LENGTH: 66
<212> TYPE: DNA
<213> ORGANISM: Artificial Sequence
<220> FEATURE:
<223> OTHER INFORMATION: Primer for light chain, linker, and s-tag
      smplification forward primer

<400> SEQUENCE: 14
ggaggcggtg gatcgggcgg tggcggctcg ggtggcggcg gctctgaaaa tgtgctcacc    60
cagtct                                                               66

<210> SEQ ID NO 15
<211> LENGTH: 78
<212> TYPE: DNA
<213> ORGANISM: Artificial Sequence
<220> FEATURE:
<223> OTHER INFORMATION: Primer for light chain, linker, and s-tag
      amplification reverse primer

<400> SEQUENCE: 15
agtcaggcta gcttagctgt ccatgtgctg gcgttcgaat ttagcagcag cggtttcttt    60
cgctttcagc tccagctt                                                  78

<210> SEQ ID NO 16
<211> LENGTH: 15
<212> TYPE: PRT
<213> ORGANISM: Unknown
<220> FEATURE:
<223> OTHER INFORMATION: Peptide of s-tag or s-peptide

<400> SEQUENCE: 16

Lys Glu Thr Ala Ala Ala Lys Phe Glu Arg Gln His Met Asp Ser
1               5                   10                  15

<210> SEQ ID NO 17
<211> LENGTH: 16
<212> TYPE: PRT
<213> ORGANISM: Unknown
<220> FEATURE:
<223> OTHER INFORMATION: ENOX2 from Table II

<400> SEQUENCE: 17

Glu Glu Met Thr Glu Thr Lys Glu Thr Glu Glu Ser Ala Leu Val Ser
```

```
<210> SEQ ID NO 18
<211> LENGTH: 16
<212> TYPE: PRT
<213> ORGANISM: Unknown
<220> FEATURE:
<223> OTHER INFORMATION: Alpha-antitrypsin inhibitor from Table II

<400> SEQUENCE: 18

Gly Thr Asp Cys Val Ala Lys Glu Ala Thr Glu Ala Ala Lys Cys Asn
1               5                   10                  15

<210> SEQ ID NO 19
<211> LENGTH: 16
<212> TYPE: PRT
<213> ORGANISM: Unknown
<220> FEATURE:
<223> OTHER INFORMATION: Serrotransferrin from Table II

<400> SEQUENCE: 19

Cys Leu Asp Gly Thr Arg Lys Pro Val Glu Glu Tyr Ala Asn Cys His
1               5                   10                  15

<210> SEQ ID NO 20
<211> LENGTH: 5
<212> TYPE: PRT
<213> ORGANISM: Unknown
<220> FEATURE:
<223> OTHER INFORMATION: ENOX2 from Table II

<400> SEQUENCE: 20

Glu Glu Met Thr Glu
1               5
```

METHODS FOR SINGLE CHAIN VARIABLE REGION ENOX2 ANTIBODIES FOR CANCER DETECTION AND DIAGNOSIS

CROSS-REFERENCE TO RELATED APPLICATIONS

This patent application is a divisional of U.S. application Ser. No. 14/229,091, which is a continuation of International Patent Application No. PCT/US2012/059141, filed Oct. 5, 2012 which claims the benefit of U.S. Provisional Application No. 61/543,931, filed Oct. 6, 2011, each of which is hereby incorporated by reference.

BACKGROUND OF THE INVENTION

The field of this invention is the area of protein biochemistry, in particular, as related to the diagnosis of neoplastic and diseased cells, as specifically related to particular isoforms of a cell surface marker characteristic of neoplasia in general and with specific patterns of protein expression indicative of specific types of cancer. Detection of the particular isoforms is by use of specific antibodies.

There is a unique, growth-related family of cell surface hydroquinone or NADH oxidases with protein disulfide-thiol interchange activity referred to as ECTO-NOX proteins (for cell surface NADH oxidases) (Morre, 1998. Plasma Membrane Redox Systems and Their Role in Biological Stress and Disease (Asard, H., Berczi, A. and Caubergs, R. J., Eds) pp. 121-156, Kluwer Academic Publishers, Dordrecht, Netherlands; Morre and Morre, 2003. Free Radical Res. 37: 795-805). One member of the ECTO-NOX family, designated ENOX2 (for tumor associated) is specific to the surfaces of cancer cells and the sera of cancer patients (Morre et al., 1995. Proc. Natl. Acad. Sci. 92: 1831-1835; Bruno et al., 1992. Biochem. J. 284: 625-628). The presence of the ENOX2 protein has been demonstrated for several human tumor tissues (mammary carcinoma, prostate cancer, neuroblastoma, colon carcinoma and melanoma) (Cho et al., 2002. Cancer Immunol. Immunother. 51: 121-129); and serum analysis suggest a much broader association with human cancer (Morre, et al., 1997. Arch. Biochem. Biophys. 342: 224-230; Morre and Reust, 1997. J. Bioenerg. Biomemb. 29: 281-289).

NOX proteins are ectoproteins anchored in the outer leaflet of the plasma membrane (Morre, 1965. Biochim. Biophys. Acta 1240: 201-208; FIG. 1). As is characteristic of other examples of ectoproteins (sialyl and galactosyl transferase, dipeptidylamino peptidase IV, etc.), the NOX proteins are shed. They appear in soluble form in conditioned media of cultured cells (Cho et al., 2002. Cancer Immunol. Immunother. 51: 121-129) and in patient sera (Morre, et al., 1997. Arch. Biochem. Biophys. 342: 224-230; Morre and Reust, 1997. J. Bioenerg. Biomemb. 29: 281-289). The serum form of ENOX2 from cancer patients exhibits the same degree of drug responsiveness as does the membrane-associated form. Drug-responsive ENOX2 activities are seen in sera of a variety of human cancer patients, including patients with leukemia, lymphomas or solid tumors (prostate, breast, colon, lung, pancreas, ovarian, liver) (Morre, et al., 1997. Arch. Biochem. Biophys. 342: 224-230; Morre and Reust, 1997. J. Bioenerg. Biomemb. 29: 281-289). An extreme stability and protease resistance of the ENOX2 protein (del Castillo-Olivares et al., 1998. Arch. Biochem. Biophys. 385: 125-140) may help explain its ability to accumulate in sera of cancer patients to readily detectable levels. In contrast, no drug-responsive NOX activities have been found in the sera of healthy volunteers (Morre, et al., 1997. Arch. Biochem. Biophys. 342: 224-230; Morre and Reust, 1997. J. Bioenerg. Biomemb. 29: 281-289) or in the sera of patients with disorders other than neoplasia.

While the basis for the cancer specificity of cell surface ENOX2 was not previously determined, the concept was supported by several lines of evidence. A drug responsive ENOX2 activity has been rigorously determined to be absent from plasma membranes of non-transformed human and animal cells and tissues (Morre et al., 1995. Proc. Natl. Acad. Sci. 92: 1831-1835). The ENOX2 proteins lack a transmembrane binding domain (Morre, et al., 2001. Arch. Biochem. Biophys. 392: 251-256) and are released from the cell surface by brief treatment at low pH (del Castillo-Olivares et al., 1998. Arch. Biochem. Biophys. 358: 125-140). A drug-responsive ENOX2 activity has not been detected in sera from healthy volunteers or patients with diseases other than cancer (Morre, et al., 1997. Arch. Biochem. Biophys. 342: 224-230; Morre and Reust, 1997. J. Bioenerg. Biomemb. 29: 281-289).). Several ENOX2 antisera have identified the immunoreactive band at 34 kDa (the processed molecular weight of one of the cell surface forms of ENOX2) with Western blot analysis or immunoprecipitation when using transformed cells and tissues or sera of cancer patients as antigen source (Cho et al., 2002. Cancer Immunol. Immunother. 51: 121-129; Morre, et al., 2001. Arch. Biochem. Biophys. 392: 251-256; Chueh et al., 2002. Biochemistry 44: 3732-3741). The immunoreactive band at 34 kDa is absent with western blot analysis or immunoprecipitation when using transformed cells and tissues or sera from healthy volunteers or patents with disorders other than cancer (Cho et al., 2002. Cancer Immunol. Immunother. 51: 121-129; Morre, et al., 2001. Arch. Biochem. Biophys. 392: 251-256; Chueh et al., 2002. Biochemistry 44: 3732-374). These antisera include a monoclonal antibody (Cho et al., 2002. Cancer Immunol. Immunother. 51: 121-129), single-chain variable region fragment (scFv) which reacts with the cell surface NADH oxidase from normal and neoplastic cells, polyclonal antisera made in response to expressed ENOX2 (Chueh et al., 2002. Biochemistry 44: 3732-374) and polyclonal peptide antisera to the conserved adenine nucleotide binding region of ENOX2 (Chueh et al., 2002. Biochemistry 44: 3732-374).

ENOX2 cDNA has been cloned (GenBank Accession No. AF207881; 11; U.S. Patent Publication 2003-0207340 A1). The derived molecular weight from the open reading frame was 70.1 kDa. Functional motifs include a quinone binding site, an adenine nucleotide binding site, and a cysteine pair as a potential protein disulfide-thiol interchange site based on site-directed mutagenesis (Chueh et al., 2002. Biochemistry 44: 3732-374). Based on available genomic information (Bird, 1999. Direct submission of human DNA sequence from clone 875H3 (part of APK1 antigen) to GenBank database at NCBI) the ENOX2 gene is located on chromosome X, and it is comprised of multiple exons (thirteen). It is known that there are a number of splice variant mRNAs and proteins expressed.

The hybridoma cell line which produces the tumor NADH oxidase-specific monoclonal antibody MAB 12.1 was deposited with the American Type Culture Collection, Manassas, Va., 20108 on Apr. 4, 2002, under the terms of the Budapest Treaty. This deposit is identified by Accession No. ATCC PTA-4206. The deposit will be maintained with restriction in the ATCC depository for a period of 30 years from the deposit date, or 5 years after the most recent request, or for the effective life of the patent, whichever is longer, and will be replaced if the deposit becomes nonviable during that period. This monoclonal antibody is described in U.S. Pat. No. 7,053,188, issued May 30, 2006, which is incorporated by reference herein.

Because cancer poses a significant threat to human health and because cancer results in significant economic costs, there is a long-felt need in the art for an effective, economical and technically simple system in which to assay for the presence of cancer.

BRIEF SUMMARY OF THE INVENTION

The present invention provides a method for the analysis of a biological sample for the presence of particular isoforms of the pan-cancer antigen known as ENOX2 (for tumor-specific NADH oxidase). The present method entails 2-dimensional gel electrophoresis and immunoblotting using an antibody specific for the pan-cancer ENOX2 antigen and the various isoforms which characterize particular types of cancers. As specifically exemplified, about 30 μL of sera are loaded for analysis.

The present invention provides a method for the detection of particular cancer-specific serum or plasma ENOX2 isoforms as indicators of the presence of cancer and of the cell type or tissue of cancer origin (breast, ovarian prostate, etc.). ENOX2 isoforms are identified on the basis of their molecular mass and isoelectric point with detection using a ENOX2-specific monoclonal antibody (MAB) (U.S. Pat. No. 7,053,188), using single chain variable region (ScFv) fragment which recognizes all cell surface NOX proteins (both age-related, normal cell and neoplasia specific NADH oxidase) or using polyclonal sera raised against ENOX2. The ECTO-NOX proteins are first enriched and concentrated from a biological sample, desirably a serum sample, by binding to nickel-agarose and then eluting. After release of the proteins from the nickelagarose by vortexing, the proteins are separated in the first dimension by isoelectric focusing and in the second dimension by polyacrylamide gel electrophoresis. As specifically exemplified herein, the isoelectric focusing step is over a pH range from 3 to 10, and size separation is over a 10% polyacrylamide gel. Most of the cancer-specific ENOX2 isoforms exhibit isoelectric points in a very narrow range between pH 3.9 and 6.3 but differ in molecular weight from 34 to 136 kDa. In the 2D gel system specifically exemplified, the cancer-specific isoforms are located in Quadrants I (relatively high molecular weight material) and IV (lower molecular weight material, notably the range of 30 to 30 kDa. IgG heavy chains (Quadrant II and IgG light chains (Quadrant III) cross react with the ScFv antibody and along with reference proteins at 53 and 79 to 85 kDa serve as loading controls. The absence of all ENOX2 isoforms indicates the absence of cancer. The presence of an ENOX2 isoform indicates the presence of cancer. The particular molecular weight present in a serum sample or a particular combination of isoforms provides an indication of the cell type or tissue of origin of the cancer. The method not only determines cancer presence, but also the method of the present invention provides diagnostic information concerning the tissue of origin. At present there are no other pan cancer (all forms of human cancer) tests with these particular capabilities.

The present invention provides a method for determining neoplasia in a mammal, including a human, said method comprising the steps of detecting cancer presence, in a biological sample. The present invention further provides additional information for assessment of neoplasia, including a measure of tumor burden, for example in serum, plasma, urine, saliva or in biopsy material.

Also within the scope of the present invention are particular isoforms of ENOX2 associated with specific (primary) cancers. ENOX2 proteins with apparent molecular weights of about 64, 66 and/or 68 kDa. pH 4.5 are associated with breast cancer. ENOX2 protein of 52 kDa, pH 4.3 is associated with small cell lung cancer. ENOX2 proteins of 52 and 80 kDa, pH 4.1 and 4.2 characterize ovarian cancer. ENOX2 isoforms of about 75 kDa, pH 6.3 are associated with prostate cancer. An ENOX2 protein of about 94 kDa, pH 5.4 is associated with cervical cancer. ENOX2 proteins of about 34 and 52 kDa, pH 4.3 and 3.9 are characteristic of colon cancer. An ENOX2 isoform of 54 kDa, pH 5.1 is associated with non small cell lung cancer. Where a patient is suspected of having cancer, a biological sample, advantageously a serum sample can be prepared, and the 2D gel electrophoresis/immunological analysis of the present invention can be undertaken. Positive results are indicative of the presence of cancer, and the detection of characteristic proteins allow a presumption as to the primary incidence of cancer in that patient according to the association of particular protein(s) with particular cancer origins, as set forth above.

The methods of the present invention can also be applied to evaluate response to therapy, with decreasing amounts of NOX isoform(s) reflecting successful treatment, as well as early detection of recurrent disease (reflected increased or reappearance of ENOX2-specific isoforms).

Specifically the invention teaches the structure, epitope characterization, binding affinity, specificity of the antigens to which the recombinant detecting antibodies must bind.

BRIEF DESCRIPTION OF THE DRAWINGS

FIG. 3A. Cervical cancer. FIG. 3B. Ovarian cancer. FIG. 3C. Prostate cancer. FIG. 3D. Breast cancer. FIG. 3E. Non-small cell lung cancer. FIG. 3F. Small cell lung cancer. FIG. 3G. Pancreatic cancer. FIG. 3H. Colon cancer. FIG. 3I. Non-Hodgkins lymphoma. FIG. 3J. Melanoma. The approximate location of unreactive (at background) albumin (Ab) is labeled for comparison. Approximately 180 non-cancer patient sera were analyzed in parallel without evidence of proteins indicative of specific transcript variants.

FIGS. 5A-5E show 2-D gel electrophoretic separations and detection of ENOX2 transcript variants specific for breast cancer by western blotting of patient sera in FIGS. 5A-5E. Arrow=66 to 68 kDa breast cancer specific transcript variant. R=52 kDa, isoelectric point pH 4.1 α1-antitrypsin inhibitor reference spot.

DETAILED DESCRIPTION OF THE INVENTION

The cancer diagnostic system of the present invention utilizes two-dimensional polyacrylamide gel electrophoretic techniques for the separation of proteins in human sera to generate cancer-specific isoform patterns and compositions indicative of cancer presence, tumor type, disease severity and therapeutic response. The protocol is designed for the detection of at least 20 cancer-specific ENOX2 isoforms which are resolved to indicate cancer presence and disease severity. This specification illustrates the process of the isoform-resolving two-dimensional gel electrophoresis protocol and subsequent immunoanalysis to detect ENOX2 isoforms which reflect particular cancers.

Two-dimensional gel electrophoresis separates by displacement in two dimensions oriented at right angles to one another and immunoblotting identifies the ENOX2 isoforms. In the first dimension isoforms are separated according to charge (pI) by isoelectric focusing (IEF). The isoforms are then separated according to size (Mr) by SDS-PAGE in a second dimension. The isoforms are then blotted onto a nitrocellulose membrane for further analysis using a pan-cancer specific antibody preparation.

Figure 1:
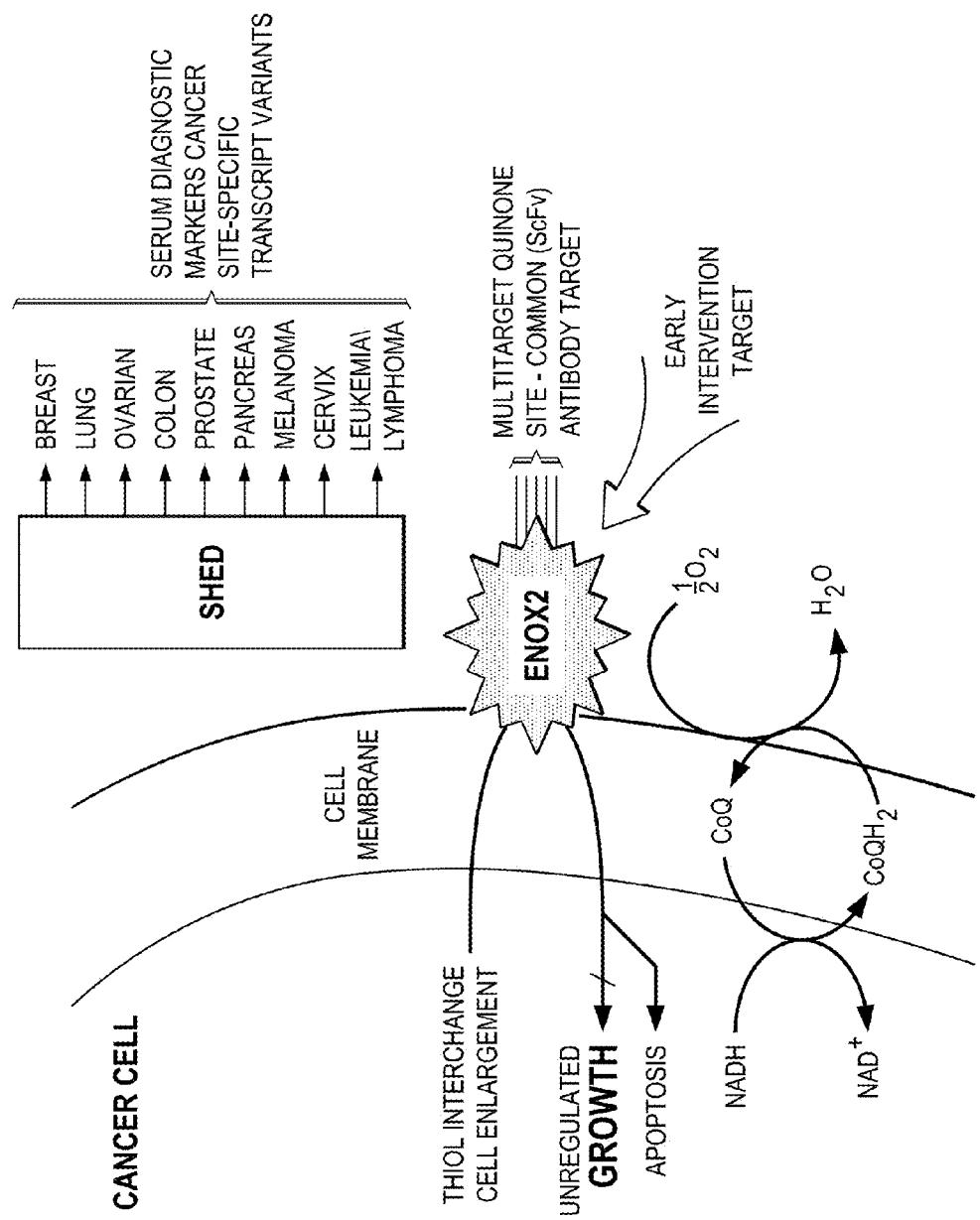
FIG. 1 is a schematic representation of the utility of the ENOX2 family of cancer-specific, cell surface proteins for early diagnosis and early intervention of cancer. Cancer site-specific transcript variants of ENOX2 are shed into the serum to permit early detection and diagnosis. The ENOX2 proteins of origin at the cell surface act as terminal oxidases of plasma membrane electron transport functions essential to the unregulated growth of cancer. When the ENOX2 proteins are inhibited, as for example through EGCg/*Capsicum* synergies, the unregulated growth ceases and the cancer cells undergo programmed cell death (apoptosis).

Ecto-Nicotinamide Adenine Dinucleotide Oxidase DisulfideThiol Exchanger 2 (ENOX2) (GenBank accession no. AF207881; Chueh et al., 2002) also known as Tumor Associated Nicotinamide Adenine Dinucleotide Oxidase (ENOX2) is ideally suited as a target for early diagnosis as well as for early preventive intervention (FIG. 1). The proteins are expressed on the cell surface of malignancies and detectable in the serum of patients with cancer (Cho et al., 2002). ENOX2 proteins are terminal hydroquinone oxidases of plasma membrane electron transport. From the standpoint of early intervention, they are important in the growth and enlargement of tumor cells (Morre and Morre, 2003; Tang et al., 2007. Biochemistry 46:12337-12346; 2008. Oncol. Res. 16:557-567). Our approach using ENOX2, as a target for both early detection and for early interventions, is based on these properties (Cho et al., 2002; Morre and Morre, 2003; reviewed by Davies and Bozzo, 2005. Drug News Perspect 19: 223-225). While ENXO2 presence provides a non-invasive approach to cancer detection, without methodology to identify cancer site-specific ENOX2 forms, it did not offer an indication as to cancer type or location.

The opportunity to simultaneously determine both cancer presence and cancer site emerged as a result of 2-dimensional gel electrophoretic separations where western blots with a pan ENOX2 recombinant single chain variable region (ScFv) antibody carrying an S tag (FIGS. 2A and 2B) was employed for detection (Hostetler et al., 2009. Clin. Proteomics 5: 46-51). The antibody cross reacted with all known ENOX2 forms from hematological and solid tumors of human origin but, of itself, did not differentiate among different kinds of cancers. Analyses using this antibody, when combined with two-dimensional gel electrophoretic separation, revealed specific ENOX2 species subsequently identified as transcript variants, each with a characteristic molecular weight and isoelectric point indicative of a particular form of cancer (Hostetler et al, 2009; Table I).

ENOX transcript variants of specific molecular weights and isoelectric points are produced uniquely by patients with cancer. The proteins are shed into the circulation and have the potential to serve as definitive, non-invasive and sensitive serum markers for early detection of both primary and recurrent cancer in at risk populations with a low incidence of false positives, as they are molecular signature molecules produced specifically by cancer cells and absent from non-cancer cells.

As the 2-D-western blot protocol detects cancer early, well in advance of clinical symptoms. The opportunity to combine early detection with early intervention as a potentially curative prevention strategy for cancer by eliminating the disease in its very earliest stages is unique.

Analytical 2-D gel electrophoresis and immunoblotting of ENOX proteins from a mixed population of cancer patients (cervical, breast, ovarian, lung and colon carcinomas, leukemias and lymphomas) revealed multiple species of acidic proteins of molecular weight between 34 and 100 kDa in quadrants I and IV (FIG. 1), none of which were present in sera of non-cancer patients (FIG. 1) (Hostetler et al., 2009). Separation in the first dimension was by isoelectric focusing over the pH range of 3 to 10 and separation in the second dimension was by 10 percent SDS-PAGE. Isoelectric points of the ENOX2 transcript variants were in the range of 3.9 to 6.3. The principal reactive proteins other than the ENOX2 forms were a 53 kDa isoelectric point pH 4.1, mostly phosphorylated α1-antitrypsin inhibitor (α2-HS-glycoprotein; fetuin A) (Labeled "R" in FIGS. 2A and 2B) which served as a convenient loading control and isoelectric point reference and a 79-85 kDa, isoelectric point pH 6.8 serotransferrin which served as a second point of reference for loading and as an isoelectric point reference (Table II). The two cross reactive reference proteins are present in a majority of sera and plasma of both cancer and non-cancer subjects. Albumin and other serum proteins do not react. On some blots, the recombinant scFv was weakly cross-reactive with heavy (ca. 52 kDa) and light (ca. 25 kDa) immunoglobulin chains.

Figures 2A, 2B:
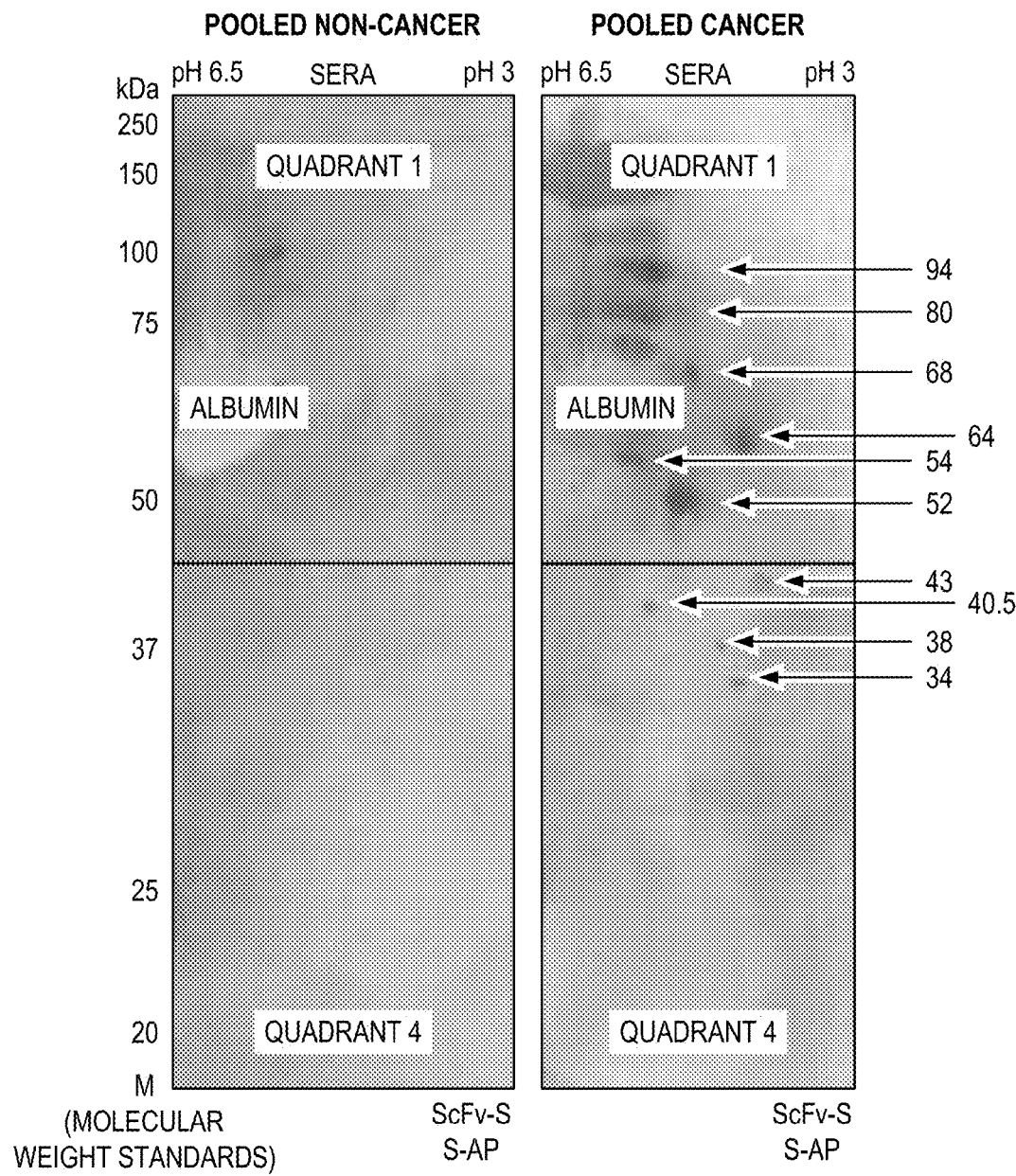
FIGS. 2A-2B provide a 2-Dimensional gel/western blot of ENOX2 transcript variants comparing pooled non-cancer (FIG. 2A) and pooled cancer representing major carcinomas plus leukemias and lymphomas (FIG. 2B) patient sera. The approximate location of unreactive (at background) albumin is labeled for comparison. ENOX2 reactive proteins are restricted to quadrants I and IV. Detection use recombinant scFv-S(S-tag peptide: His-Glu-Ala-Ala-Lys-Phe-Gin-Arg-Glu-His) antibody linked with alkaline phosphatase. The approximately 10 ENOX2 transcript variants of the pooled cancer sera are absent from non-cancer (A) and are cancer site-specific.
Figures 3A, 3B, 3C, 3D, 3E, 3F, 3G, 3H, 3I, 3J:
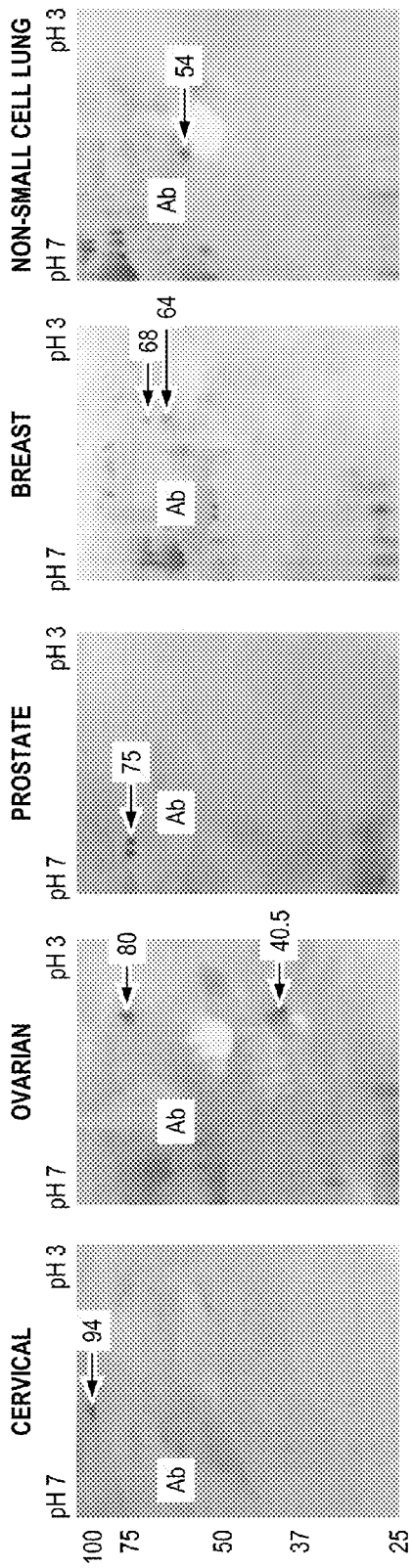
FIGS. 3A-3J show western blots of 2-D gel electrophoresis/western blots of sera from cancer patients analyzed individually. Cancer sites are presented in the order of decreasing molecular weight of the major transcript variant present.
Figure 4A:
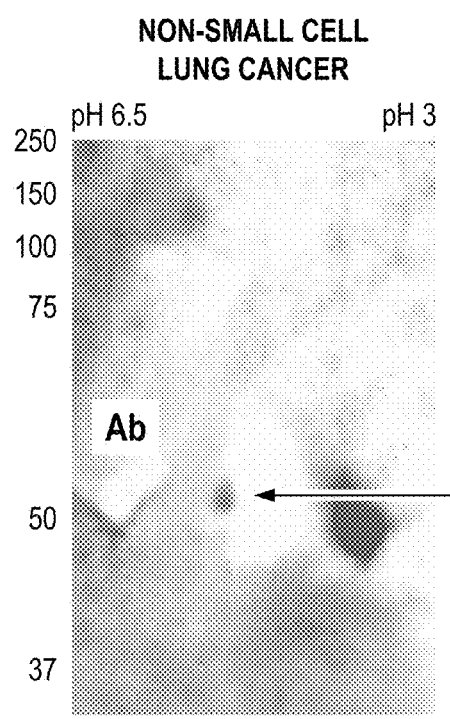
FIGS. 4A-4B show analytical gel electrophoresis and immunoblots of patient sera. A. Sera from a patient with non-small cell lung cancer contains a 54 kDa, isoelectric point pH 5.1 transcript variant (arrow). B. Sera from a patient with small cell lung cancer contains a 52 kDa, isoelectric point 4.3 transcript variant (arrow). The reference spots to the right, Mr 52 kDa and isoelectric point pH 4.1 are α1-antitrypsin inhibitor. Albumin and other serum proteins are unreactive.
Figure 4B:
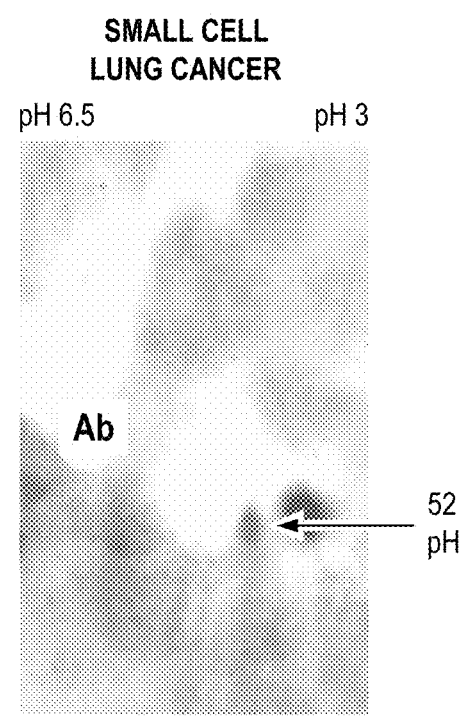

Sera from individual patients with various forms of cancer were analyzed by 2-D gel electrophoresis and immunoblotting to assign each of the ENOX2 isoforms of FIGS. 2A and 2B to a cancer of a particular tissue of origin (Table 1). Sera of breast cancer patients contained only the 64 to 68 kDa ENOX2 (FIG. 3D) and the α1-antitrypsin inhibitor reference protein (FIGS. 3A through 3J). Sera from cervical cancer patients contained the 94 kDa ENOX2 transcript variant (FIG. 3A). Sera from ovarian cancer patients contained ENOX1 transcript variants of 80 kDa and 40.5 b kDa (FIG.

3B). Sera from patients with prostate cancer contained one or more 75 kDa ENOX2 transcript variants resulting in small variations in isoelectric points (FIG. 3C). Sera from patients with non-small cell lung carcinoma contained a 52 kDa ENOX2 transcript variant while sera from non-small cell lung carcinoma patients contained a of 52 kDa ENOX2 transcript variant (FIGS. 3E and 3F and FIGS. 4A and 4B). ENOX2 transcript variants of 50 and 52 kDa characterized sera of pancreatic cancer patients (FIG. 3G) whereas sera of colon cancer patients contained ENOCX2 transcript variants of 52 kDa and 43 kDa (FIG. 3H). FIG. 3I from sera of a patient with non-Hodgkin's lymphoma illustrates the 45 kDa ENOX2 transcript variant of low isoelectric point characteristic of leukemias and lymphomas. Sera of patients with malignant melanoma contained an ENOX2 transcript variant of 38 kDa (FIG. 3J).

Particularly relevant are observations where the 64 to 68 kDa ENOX2 transcript variant (pH 4.5) of sera correlated with disease presence in both late (Stage IV) (FIG. 5A) and early (Stage I) (FIG. 5F) disease and in Stage IV recurrence (FIG. 5C) but was absent from sera of non-cancer (normal) volunteers (FIG. 5B) or in survivors free of disease for one to five years (FIG. 5D). Additionally, the 64 to 68 kDa breast cancer-specific transcript variant does not apply to a subset of breast cancer patients but appears to be universally present. Analyses of sera of more than 60 patients with active disease including 20 Stage I and Stage II breast cancer patients all tested positive.

Unlike most published cancer markers, cancer-specific ENOX2 variants are not simply present as elevated levels of a serum constituent present in lesser amounts in the absence of cancer. The cancer-specific ENOX2 transcript variants result from cancer-specific expression of alternatively spliced mRNAs (Tang et al., 2007; 2008). Neither the splice variant mRNAs nor the ENOX2 isoform proteins are present in detectable levels in non-cancer cells or in sera of subjects without cancer (Table I).

Figure 6:
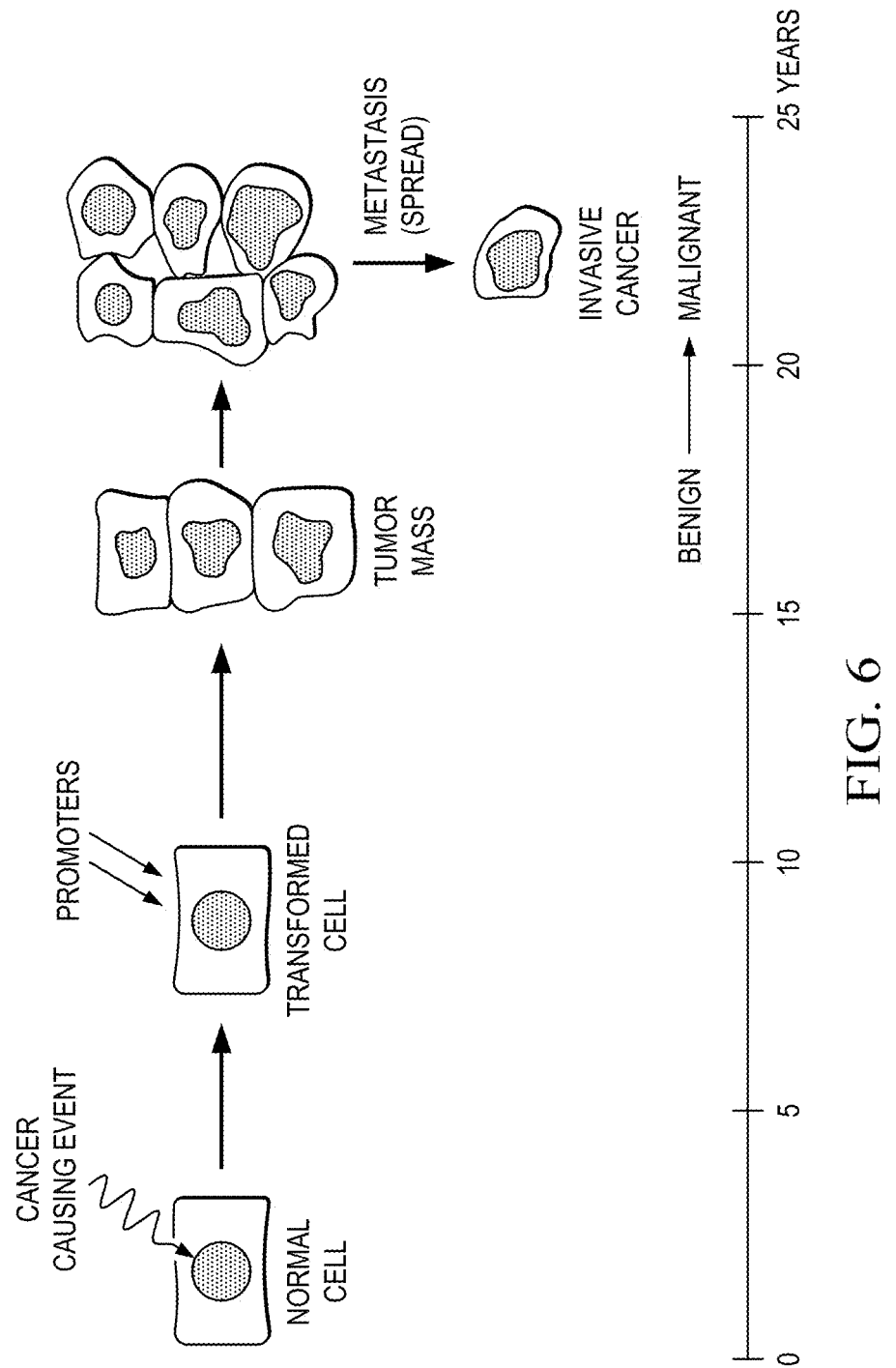
FIG. 6 is an interpretive diagram to illustrate the various stages of cancer progression (estimated to require as long as 20 y) beginning with a cancer-causing event (initiation) through development of a clinically defined malignancy.

Findings from a separate study with small cell and non-small cell lung cancer suggest that the 2-D-western blot test detects cancer presence 5 to 7 years in advance of the appearance of clinical symptoms. This supposition is based mainly on our analysis of two special cancer panels of sera obtained through the Early Detection Research Network (EDRN) of the National Cancer Institute. One panel consisted of about 20 known lung cancer patient sera and 35 control patient sera. Using the 2-D-western blot protocol to identify specific ENOX2 isoforms, we successfully identified all 20 of the known lung cancer patient sera. However, unexpectedly a high incidence of ENOX2 presence was encountered in sera from the "control" group which were obtained from a community screening study. From additional information obtained through the EDRN, 16 of the 17 positive control subject samples where our findings specifically indicated lung cancer (the lung cancer ENOX2 markers were found) were smokers with smoking histories in the range of 15 to 88 pack-years. However, the anticipated incidence of undetected lung cancers in such a population would be in the order of 10% or less rather than nearly 50%. Since the aberrant ENOX2 transcript variants associated with lung cancer, are single molecular species produced only by lung cancer, the possibility was raised that lung cancer was being detected much earlier than was currently possible by other methods. The indications might be as early as 5 to 7 years before clinical symptoms, based on the estimated 20 year development time for lung cancer expression between carcinogen exposure and a clinically evident cancer (Petro et al., 2000. Br. Med. J. 231: 323-329) as diagrammed in FIG. 6.

Similar results were obtained with a panel of female subjects at risk for breast and ovarian cancer. An analysis of a panel of 127 sera in a Biomarker Reference Set for Cancers in Women also provided through the Early Detection Research Network of the National Cancer Institute support our indications that the 2-D gel-western blot system is able to detect cancer presence 5 to 7 years in advance of clinical symptoms. The panel consisted of samples pooled form 441 women in 12 different gynecologic and breast disease categories plus 115 sera from age-matched control women. Of the 127 sera samples in the panel 29 tested positive for breast cancer and another 16 tested positive for ovarian cancer. Since the aberrant transcript variants are single molecular species produced by specific cancers such as lung, breast or ovarian, the findings suggest that cancer was being detected in the control population much earlier than is currently possible by other methods. As estimated for lung cancer, the indications might be as early as 5 to 7 years before clinical symptoms based on the estimated development time estimated for breast as well as lung cancer expression between a cancer causing event and clinically evident disease (Weinberg, 2007. The Biology of Cancer, Garland Science).

Many cancers are detected only after clinical symptoms present and often after the cancer has spread leaving chemotherapy as perhaps the only resource for treatment. Tomographic or x-ray methods may detect before clinical symptoms present but only after a tumor mass has already formed. There appear to be few, if any, on-going indications of opportunities either for early cancer detection or for early intervention. Various genomic, transcriptomic and/or proteomic analyses, while of potential utility for tissue analyses of biopsy material, have thus far failed to provide new and reliable non-invasive serum indicators of cancer occurrence (Goncalves and Bertucci, 2011. Med. Prin. Pract. 204: 4-18) despite continued promise offered by circulating microRNAs (Wu et al., 2011. J. Biomed. Biotechnol. Article ID 597145). A relatively small percentage of all cancers can be attributed to predisposing genes such as BRACA1, BRACA2 and less frequently p53 and PTEN (Lee et al., 2010. Breast Cancer Res. Treat. 122: 11-25) for 5 to 10% of all breast cancers. While indicative of cancer risk, predisposing genes do not necessarily signal cancer presence.

Table I shows that sera from patients with different cancers exhibit distinct patterns of ENOX2 isoforms with characteristic molecular weight and isoelectric points (pH). Updated from Hostetler et al. (2009).

| Cancer | Sera analyzed | Molecular weight | Isoelectric point, pH |
|---|---|---|---|
| Cervical | 18 | 94 kDa | 5.4 |
| Ovarian | 41 | 80 and 40.5 kDa | 4.2 and 4.1 |
| Prostate | 70 | 75 kDa | 6.3 |
| Breast/Uterine | 55 | 64 to 68 kDa | 4.5 |
| Non-small cell lung | 83 | 54 kDa | 5.1 |
| Small cell lung | 22 | 52 kDa | 4.3 |
| Pancreatic | 24 | 50 kDa | 4.3 |
| Colon | 55 | 52 and 34 kDa | 4.3 and 3.9 |
| Lymphoma, Leukemia | 16 | 45 kDa | 3.9 |
| Melanoma | 12 | 38 kDa | 5.1 |

Table II provides protein sequence similarity between ENOX2 and the two reference proteins α1-anti-trypsin inhibitor and serrotransferrin reactive with the pan ENOX2 scFv recombinant antibody. Regions of similarity are restricted to a 7 amino acid sequence (underlined) adjacent in ENOX2 to the EEMTE SEQ ID NO. 20 quinone inhibitor-binding site which serves as the antigen sequence to which the specific scFv antibodies bind.

| | (SEQ ID NO: 17) |
|---|---|
| ENOX2 | EEMTETKETEESALVS |
| | (SEQ ID NO: 18) |
| α-antitrypsin inhibitor | GTDCVAKEATEAAKCN |
| | (SEQ ID NO: 19) |
| Serrotransferrin | CLDGTRKPVEEYANCH |

Details of Method
A. Sample Preparation
 1. Prepare/thaw re-hydration solution (−20, 1.5 mL tube labeled RB)
  a. Add 1% Dithiothreitol (DTT) to solution before use (0.01 g/1.0 mL)
 2. Add 120 µL of Rehydration Buffer to a 1.7 ml tube
 3. Add 30 µL of sera to tube
 4. Vortex solution until fully mixed
 5. Remove Immobiline DryStrips from freezer (−20° C., pH 3-10) and allow strips to equilibrate to RT for 5 minutes.
  a. Do not leave strips at RT for more than 10 min.
 6. Record ID# from strip
 7. Load 130 µL of sample to tray per 7 cm DryStrip. Ensure tray is level.
 8. Place DryStrips gel-side down over sample
 9. Ensure sample is evenly spread throughout strip by carefully lifting strip in and out of sample a few times if needed.
 10. If samples are concentrated in one region of the strip, redistribute sample by pipetting.
 11. Remove air bubbles by gently pressing down on Dry Strip with pipette tip.
 12. Place lid on tray and place tray in plastic bag with ddi-H$_2$O soaked paper towels.
 13. Seal bag.
 14. Allow sample to re-hydrate overnight at RT on a level surface allowing strips to absorb sample for 12-24 hrs.
B. Isoelectric Focusing (First Dimension)
 1. Turn on IPGphor (ensure proper startup of machine)
 2. Place strips on Manifold focusing tray as follows
  a. Gel side up
  b. Positive (acidic) end towards back
  c. Strips are aligned
  d. Between metal strips (so electrodes fit and touch metal strip)
 3. Obtain 2 Paper Wicks per strip
 4. Wet wicks with 150 µL ddi-H$_2$O per wick.
 5. Place wicks over anodic and cathodic ends of gel (approx. 0.3 cm).
 6. Place electrodes on wicks, but away from gel (be sure prong is on metal plate), and lock in place.
 7. Cover strips with DryStrip Cover fluid
  a. Fill strips entire lane with oil
  b. Ensure strips are fully covered
 8. Close lid
 9. IEF run with IPGphor II
  a. Maximum amperage: 50 µAmps
  b. Temperature: 20° C.
  c. Ensure correct assembly by checking initial voltage
  d. As needed, pause run and replace wicks, continue run until dye front disappears.

| | Step | Voltage | Time/Vhrs |
|---|---|---|---|
| 7 cm Strip pH 3-10 | 1 - Stp. | 250 V | 250 Vhrs. |
| (Run #1) | 2 - Stp. | 500 V | 500 Vhrs. |
| | 3 - Stp. | 1000 V | 1000 Vhrs. |
| | 4 - Grd. | 4000 V | 3 hrs. |
| | 5 - Stp. | 4000 V | 25,000 Vhrs. |
| | 6 - Stp. | 500 V | Hold |

C. Prepare SDS-Page Gels (for Second Dimension)
 1. Prior to use, wash and scrub plates very well in soap and hot water.
 2. Rinse in diH$_2$O.
 3. Leave the plates to air dry or wipe with ethanol-soaked Kimwipes.
 4. Order plates in Protean-plus Multi-Gel casting Chamber (Bio-Rad) as per manual (with a spacer between each plate and block).
 5. Ensure screws are fully tightened.
 6. Add gel solution
 7. Stop pouring when gel is about 1-1.5 cm from top of glass plates.
 8. Gently overlay gels with ethanol
 9. Cover with Saran Wrap.
 10. Allow gels to polymerize for at least one hour (best if overnight)
D. Equilibration (First Dimension)
 1. Remove strips from tray and place on Kimwipe to remove excess oil.
 1. Place strips gel side up on Kimwipe
 2. Overlay strips with a second Kimwipe and gently blot to remove oil.
 2. Place strips in equilibration plate gel side up; freeze or equilibrate.
 1. Freeze: Wrap plate in plastic wrap, store at −80° C.
  i. Thaw strips prior to equilibration (clear when thawed).
 2. Equilibrate: continue to next step
 3. Cover strips with equilibration buffer, about 1.5 mL per strip.
 4. Heat up Agarose until it is liquefied
 5. Shake 20 min at RT
E. SDS-PAGE (Second Dimension)
 1. Prepare left (pH 10 side) markers by adding 8 µL of standards on Whatman 3 MM chromatography paper cut to about 3 cm×0.75 cm.
 1. Standards should be added to bottom of paper, about 1 cm high.
 2. Prepare right (pH 3 side) markers by adding 8 µL of standards on Whatman 3 MM chromatography paper cut to approximately 3 cm×0.75
 1. Standards should be added to bottom of paper, about 1 cm high
 3. Pour off Equilibration Buffer.
 4. Cover strips in SDS Running buffer to rinse away excess Equilibration Buffer.
 5. Remove SDS Running buffer from strips.
 6. Repeat SDS Running buffer rinse.
 7. Carefully place strips gel side out on back plate of SDS-PAGE gel.
 8. Overlay strips with 1% low melting agarose once it has cooled enough to touch skin
 1. Ensure no air bubbles have formed under the gel.
 2. Use ruler to tap gel and remove air bubbles.
 9. Insert marker's next to appropriate end of IEF strip, ensuring marker is flush to the gel on the strip
 10. Allow polymerization of agarose
 11. Continue for each strip to be loaded in 2$^{nd}$ dimension 12. Place gels in Dodeca tank, HINGED SIDE DOWN
13. After all gels have been put in tank, ensure gels are covered in entirety by SDS running buffer
14. 2$^{nd}$ dimension run is done at 13° C.
  1. 250 V
  2. 1-1.5 hr. (allow gel to run until gel front approaches tubing in lid of tank).
F. Protein Transfer (for Western Blot)
  1. Remove gel from Dodeca tank
  2. Cut gel to desired size
  3. Fill tray (large enough to fit gel) with transfer buffer.
  4. Place sponges in transblot cell—2 sponges per gel
  5. Fill tank with transfer buffer to allow sponges to saturate with transfer buffer
  6. Soak pre-cut transfer membrane
  7. Assemble transfer cassette as follows
    1. Black side down
    2. Sponge soaked in transfer buffer
    3. Filter paper
    4. Gel
    5. Nitrocellulose membrane—once placed on gel do not move membrane
    6. Filter Paper
    7. Sponge
  8. Ensure all air bubbles have been removed between gel and membrane
  9. Place tray in Transblot tank, black side (gel side) of tray to black tank side
  10. Transfer at 4° C. and following conditions (transfer can be done in an ice bath if needed)
    1. 90 V for 50 min.
    2. Membrane can be left in tank overnight at 4° C. after transfer.
G. Immunological Analysis for Western Blot Using ScFv with S-Tag Linked to Alkaline Phosphatase as Antibody
  1. Remove membrane from transfer
  2. Rinse membrane in 1% milk (enough to cover membrane) and block, 10 min, RT
  3. Prepare antibody solution (According to Titer instructions on Ab)
  4. Remove blocking solution (save at 4° C.)
  5. Place membrane into container with antibody solution
  6. Incubate at 4° C. overnight (usually 8-12 hr)
H. Development of Western Blot and Scanning
  1. Remove 1° antibody
  2. Wash membrane 4×
    1. Cover membrane with TBST
    2. Gently shake at RT for 5 min.
    3. Cover membrane with Western Blue
    4. Allow to develop until reference spots reach maximum intensity
  5. Stop develop by rinsing with ddi-water
  6. Dry membrane
  7. Scan membrane Solutions Used for First Dimension I. Rehydration Buffer pH 7 (25 mL):

| Chemical | Amount Added | Molar Mass (g/mol) | Final Value |
|---|---|---|---|
| Urea | 10.51 g | 60.06 | 7M |
| Thiourea | 3.81 g | 76.12 | 2M |
| CHAPS | 0.5 g | 614.88 | 2% |
| asb-14 | 0.125 g | 434.68 | 0.5% |
| 40% Ampholytes | 330 μL | N/A | 0.5% |
| IPG Buffer | 125 μL | N/A | 0.5% |
| ddi-H$_2$O | To 25 mL | 18.002 | N/A |
| Bromophenol Blue | 3 mg | 669.96 | 0.012% |

Dissolve Urea in minimal ddi-H2O(do not heat over 30° C.).
Dissolve Thiourea in Urea/ddi-H$_2$O solution, and then add remaining chemicals.
Q.S. with to 25 mL and aliquot to 1 mL tubes and store at −80° C.
Add 1% DTT - 10 mg (0.01 g) before use.

Solutions Used for Second Dimension

Tris Buffer (1.5 M, pH 8.8) (1 L):

| Chemical | Amount Added | Molar Mass (g/mol) | Final Value |
|---|---|---|---|
| Trizma | 181.65 g | 121.14 | 1.5M |
| HCl | pH to 8.8 | 36.46 | N/A |
| ddi-H$_2$O | To 1 L | 18.02 | N/A |

Dissolve Trizma in 750 mL and adjust pH to 8.8 with HCl.
Q.S. to final volume of 1 L with ddi-H$_2$O and store at 4° C.

Equilibration Buffer (400 mL):

| Chemical | Amount Added | Molar Mass (g/mol) | Final Value |
|---|---|---|---|
| Tris-Buffer (1.5M, pH 8.8) | 134 mL | N/A | 0.5M |
| Urea | 144.14 g | 60.06 | 6M |
| Glycerol | 120 mL (150 g) | 92.09 | 30% |
| SDS | 10 g | 288.38 | 2.5% |
| ddi-H$_2$O | To 400 ml | 18.02 | N/A |
| Bromophenol Blue | Trace amount | 669.96 | N/A |

Q.S. to final volume of 4 L with ddi-H$_2$O.
Add Bromophenol Blue (add with pipette tip to give trace of blue).
Aliquot to 15 mL tubes and store at −20° C.

Acrylamide Gel (20×20; 1-mm Thick)

| Gel % | # gels | Tris Buffer 1.5M, pH 8.8 (mL) | 30% Acrylamide (mL) | ddi-H$_2$O (mL) | 10% APS (mL) | TEMED (mL) |
|---|---|---|---|---|---|---|
| 10 | 6 | 100 | 133.33 | 166.67 | 4 | 0.4 |
|  | 8 | 125 | 166.67 | 208.33 | 5 | 0.5 |
|  | 10 | 150 | 200 | 250 | 6 | 0.6 |
|  | 12 | 175 | 233.33 | 291.67 | 7 | 0.7 |

Formulations for Protean II gels.

10% APS

| Chemical | Amount Added | Molar Mass (g/mol) | Final Value |
|---|---|---|---|
| APS | 2 g | 228.18 | 10% |
| ddi-H$_2$O | To 20 mL | 18.02 | N/A |

Q.S. to final volume of 20 mL with ddi-H$_2$O.

Agarose Solution (1%):

| Chemical | Amount Added | Molar Mass (g/mol) | Final Value |
|---|---|---|---|
| Agarose | 1.5 g | N/A | 1% |
| SDS-Running Buffer | 150 mL | N/A | N/A |
| Bromophenol Blue | Trace amount | 669.96 | N/A |

Combine agarose and SDS-Run Buffer.
Microwave to heat and dissolve.
Add Bromophenol Blue (add with pipette tip to give trace of blue).

10× SDS Running Buffer (4 L):

| Chemical | Amount Added | Molar Mass (g/mol) | Final Value |
|---|---|---|---|
| Trizma | 121.2 g | 121.14 | 0.25M |
| Glycine | 576 g | 75.07 | 1.92M |
| SDS | 40 g | 288.38 | 1% |
| ddi-$H_2O$ | To 4 L | 18.02 | N/A |

Q.S. to final volume of 4 L with ddi-$H_2O$.
Solutions for Western Blot

Western Transfer Buffer (4 L):

| Chemical | Amount Added | Molar Mass (g/mol) | Final Value |
|---|---|---|---|
| Trizma | 121.2 g | 121.14 | 0.025M |
| Glycine | 57.6 g | 75.07 | 0.192M |
| Methanol | 480 mL | 32.04 | 0.12% |
| SDS | 3 g | 288.38 | .075% |
| ddi-$H_2O$ | To 4 L | 18.02 | N/A |

Q.S. to final volume of 4 L with di-$H_2O$.

Blocking Buffer (5% BSA)

| Chemical | Mass | Molar Mass (g/mol) | Final Value |
|---|---|---|---|
| BSA | 5 g | 66500 | 5% |
| $N_3Na$ | 0.2 g | 65.01 | 0.2% |
| TBST | To 100 mL | 18.02 | N/A |

Q.S. to final volume of 100 mL with TBST.

10×TBST (4 L)

| Chemical | Amount Added | Molar Mass (g/mol) | Final Value |
|---|---|---|---|
| Trizma | 48.4 g | 121.14 | 100 mM |
| NaCl | 350.6 g | 58.44 | 1.5M |
| Tween 20 | 20.6 g | 1227.54 | 0.5% |
| HCl | pH to 7.5 | 36.46 | N/A |
| ddi-$H_2O$ | To 4 L | 18.02 | N/A |

Add Trizma and NaCl to 3.5 L ddi-$H_2O$.
pH to 7.5 by HCl.
Add Tween 20.
Q.S. to 4 L with ddi-$H_2O$.

Summary of 2-D Gel Electrophoresis Western Blot Early Detection Protocol

Serum was prepared from 5 ml of blood collected by venipuncture (with tourniquet) in standard B & D 13×100 (7 ml) vacutainer clot tubes (or equivalent) with or without hemoguard closure. After approximately 30 min at room temperature to allow for clotting, the clot was pelleted by centrifugation for 5 to 10 min at 2,500 to 3,000 rpm. Clot-free serum was decanted into a clean tube, labeled and analyzed fresh or stored frozen.

For western blot analysis, 30 µl of sera was added to 120 µl of Rehydration Buffer (7 M urea, 2 M thiourea, 2% (w/v) CHAPS [(3-[(3-cholamidopropyl)dimethylammonio]-1-propane-sulfonate), a nondenaturing zwitterionic detergent], 0.5% (w/v) ASB-14 (amidosulfobetaine-14, a zwitterionic detergent), 0.5% (v/v) ampholytes pH 3-10 (Bio-Rad), 0.5% (v/v) immobilized pH gradient (IPG) buffer pH 3-10 (Amersham-Pharmacia Biotech) and 65 mM dithiothreitol). The samples were quickly vortexed to mix sera with Rehydration Buffer. Four to six mg of protein were loaded for analysis. The samples were electrophoresed in the first dimension by using a commercial flatbed electrophoresis system (Ettan IPGphor 3, Amersham-Pharmacia Biotech) with IPG dry strips (Amersham). A linear pH range of 3 to 10 on 7 cm IPG strips was used. The IPG strips were rehydrated with the samples overnight at room temperature. The strips were then focused at 50 mA per strip and at increasing voltage of 250 V for 250 Vhrs, 500 V for 500 Vhrs, 1,000 V for 1,000 Vhrs and 4,000 V for 3 hrs. The samples were then focused at a constant 4,000 V for 28,000 Volt-hours. After isoelectric focusing, the IPG strips were re-equilibrated for 20 min in 2.5% (w/v) SDS, 6 M urea, 30% (v/v) glycerol, 100 mM Tris-HCl (pH 8.8). The strips were placed onto linear SDS-PAGE gels (10% (w/v) polyacrylamide) and electrophoresed at a constant 250 V for 75 min. The samples were then transferred to nitrocellulose membranes by electroblotting using the Bio-Rad Trans-Blot Electrophoretic Transfer Cell. The membranes were blocked using milk protein (1% low fat dry milk) at room temperature for 10 min. Detection was with recombinant anti-ENOX2 single chain variable region of antibody (scFv) that was alkaline phosphatase-linked overnight at 4° C. After washing, detection was performed with Western Blue nitrotetrazolium (NBT) substrate (Promega, Madison, Wis.; Cat. No. 53841) at room temperature. Images were scanned and processed using Adobe Photoshop. Quantitation utilized an algorithm developed for this purpose. Reactive proteins appeared reddish blue. For interpretative purposes, the blots were divided into quadrants I-IV with unreactive serum albumin at the center (FIGS. 2A and 2B).

EXAMPLES

Example 1

Analysis of Sera Pooled from Cancer Patients

Example 1A. NOX-enriched serum proteins (approximately 4-6 mg) from sera pooled from cancer patients (breast, ovarian, lung and colon) were resolved by 2-D gel electrophoresis. Detection was by recombinant anti-ECTO-NOX antibody (single chain variable region ScFv) carrying an S-tag followed by alkaline phosphatase-linked anti-S with Western Blue NBT alkaline phosphatase substrate yield several proteins present in the cancer sera (FIG. 1) but absent from sera of non-cancer patients or healthy volunteers. Example 1B. The same procedure can be followed as in Example 1A, except that detection can be by recombinant anti-ECTO-NOX variable region single chain (scFv) using the scFv linked directly as described above to alkaline phosphatase (overnight at 4° C.). By using the directly linked antibody the process is less expensive and one day faster than using an S-tag followed by an anti-S tag antibody linked to alkaline phosphatase.

Example 2

Analysis of Small Cell Lung Cancer Patient Serum

Example 2A. 2-D gel analysis when applied to sera of a patient with small cell lung cancer contained a 52 kDa, pH 4.2 ENOX2 protein in quadrant I with detection using the S-tag procedure in Example 1A above. Example 2B. The same procedure can be followed as in Example 2A, except that detection can be by recombinant anti-ECTO-NOX variable region single chain (scFv) using the scFv linked directly as described above to alkaline phosphatase (overnight at 4° C.). By using the directly linked antibody the process is less expensive and one day faster than using an S-tag followed by an anti-S tag antibody linked to alkaline phosphatase.

Example 3

Analysis of Non Small Cell Lung Cancer Patient Serum

Example 3A. 2-D gel analysis as in FIG. 1 when applied to plasma from a patient with non-small cell lung cancer revealed a non-small cell cancer specific ENOX2 isoform at 54 kDa, pH 5.1 in quadrant 1 with detection using the S-tag procedure in Example 1A above. Example 3B. The same procedure can be followed as in Example 3A, except that detection can be by recombinant anti-ECTO-NOX variable region single chain (scFv) using the scFv linked directly as described above to alkaline phosphatase (overnight at 4° C.). By using the directly linked antibody the process is less expensive and one day faster than using an S-tag followed by an anti-S tag antibody linked to alkaline phosphatase.

Example 4

Analysis of Breast Cancer Patient Serum

Example 4A. 2-D gel analysis as in FIG. 1 when applied to sera from a patient with breast cancer revealed a breast cancer-specific ENOX2 protein of 68 kDa, pH 4.5 in quadrant 1 with detection using the S-tag procedure in Example 1A above. Example 4B. The same procedure can be followed as in Example 4A, except that detection can be by recombinant anti-ECTO-NOX variable region single chain (scFv) using the scFv linked directly as described above to alkaline phosphatase (overnight at 4° C.). By using the directly linked antibody the process is less expensive and one day faster than using an S-tag followed by an anti-S tag antibody linked to alkaline phosphatase.

Example 5

Analysis of Prostate Cancer Patient Serum

Example 5A. 2-D gel analysis as in FIG. 1 when applied to sera from a patient with prostate cancer revealed prostate cancer-specific ENOX2 isoforms at 75 kDa and isoelectric points of pH 6.3 with detection using the S-tag procedure in Example 1A above. Example 5B. The same procedure can be followed as in Example 5A, except that detection can be by recombinant anti-ECTO-NOX variable region single chain (scFv) using the scFv linked directly as described above to alkaline phosphatase (overnight at 4° C.). By using the directly linked antibody the process is less expensive and one day faster than using an S-tag followed by an anti-S tag antibody linked to alkaline phosphatase.

Example 6

Analysis of Cervical Cancer Patient Serum

Example 6A. 2-D gel analysis as in FIG. 1 when applied to serum from a patient with cervical cancer revealed a cervical cancer-specific ENOX2 isoform at 94 kDa, pH 5.4 with detection using the S-tag procedure in Example 1A above. Example 6B. The same procedure can be followed as in Example 6A, except that detection can be by recombinant anti-ECTO-NOX variable region single chain (scFv) using the scFv linked directly as described above to alkaline phosphatase (overnight at 4° C.). By using the directly linked antibody the process is less expensive and one day faster than using an S-tag followed by an anti-S tag antibody linked to alkaline phosphatase.

Example 7

Analysis of Colon Cancer Patient Serum

Example 7A. 2-D gel analysis as in FIG. 1 when applied to serum from a patient with colon cancer revealed colon cancer-specific ENOX2 isoforms at 38 and 52 kDa, pH 4.3 and 3.9 with detection using the S-tag procedure in Example 1A above. Example 7B. The same procedure can be followed as in Example 7A, except that detection can be by recombinant anti-ECTO-NOX variable region single chain (scFv) using the scFv linked directly as described above to alkaline phosphatase (overnight at 4° C.). By using the directly linked antibody the process is less expensive and one day faster than using an S-tag followed by an anti-S tag antibody linked to alkaline phosphatase.

Example 8

Cancer Specific Isoforms

For each kind of cancer there appears to be a ENOX2 isoform (ovarian, breast, cervical, colon, non-small cell lung, prostate small cell lung) or combination of ENOX2 isoforms that is specific to the tissue or cell type of origin for the cancer. This test is preferably done with recombinant anti-ECTO-NOX variable region single chain (scFv) using the scFv linked directly as described above to alkaline phosphatase. By using the directly linked antibody the process is less expensive and one day faster than using an S-tag followed by an anti-S tag antibody linked to alkaline phosphatase.

Example 9

Analysis of Patient Serum where Cancer of Unknown Origin

The 2-D gel of sera from a patient with cancer where the primary tumor was unknown revealed the presence of 40.5 and 80 kDa, pH 4.2 and 4.1 ENOX2 isoforms to indicate that the primary cancer was ovarian cancer (not shown).

In more than 25 randomly selected outpatient sera and sera of healthy volunteers, both quadrants I and IV of the 2-D gels were devoid of ENOX2 isoforms, confirming previous observations that ENOX2 proteins are absent from non-cancer patients or sera of healthy volunteers.

The diagnostic strategy of the invention combines one- and two-dimensional polyacrylamide gel electrophoretic separations of human sera to generate cancer specific isoform patterns and compositions indicative of cancer presence, tumor type, disease severity and therapeutic response. At least 20 cancer-specific ENOX2 isoforms are resolved indicative of cancer presence and disease severity. Detection uses a recombinant single chain antibody (scFv) that reacts with all known ECTO-NOX isoforms of human origin. While the technique can be used with an antibody that has an S-tag, the process is less expensive and faster by using the scFv linked directly to alkaline phosphatase or another suitable detection aid.

Monoclonal antibody generated against ENOX2 NADH oxidase tumor cell specific was produced in sp-2 myeloma cells; however, the monoclonal antibody slowed the growth of sp-2 myeloma cells that were used for fusion with spleen cells after 72 h. This phenomenon made it difficult to produce antibody in quantity. To overcome this problem, the coding sequences of the antigen-binding variable region of the heavy chain and the light chain (Fv region) of the antibody cDNA were cloned and linked into one chimeric gene, upstream of the S-tag coding sequence. The Fv portion of an antibody, consisting of variable heavy (VH) and variable light (VL) domains, can maintain the binding specificity and affinity of the original antibody (Glockshuber et al. 1990. Biochemistry 29:1262-1367).

For a recombinant antibody, cDNAs encoding the variable regions of immunoglobulin heavy chain (VH) and light chain (Vl), are cloned by using degenerative primers. Mammalian immunoglobulins of light and heavy chain contain conserved regions adjacent to the hypervariable complementary defining regions (CDRs). Degenerate oligoprimer sets allow these regions to be amplified using PCR (Jones et al. 1991. Bio/Technology 9:88-89; Daugherty et al. 1991. Nucleic Acids Research 19:2471-2476). Recombinant DNA techniques have facilitated the stabilization of variable fragments by covalently linking the two fragments by a polypeptide linker (Huston et al. 1988. Proc. Natl. Acad. Sci. USA 85:5879-5883). Either VL or VH can provide the NH2-terminal domain of the single chain variable fragment (ScFv). The linker should be designed to resist proteolysis and to minimize protein aggregation. Linker length and sequences contribute and control flexibility and interaction with ScFv and antigen. The most widely used linkers have sequences consisting of glycine (Gly) and serine (Ser) residues for flexibility, with charged residues as glutamic acid (Glu) and lysine (Lys) for solubility (Bird et al. 1988. Science 242:423-426; Huston et al. 1988. supra).

Total RNA was isolated from the hybridoma cells producing ENOX2-specific monoclonal antibodies by the following procedure modified from Chomczynski et al. (1987) Anal. Biochem. 162:156-159 and Gough (1988) Anal. Biochem 176:93-95. Cells were harvested from medium and pelleted by centrifugation at 450×g for 10 min. Pellets were gently resuspended with 10 volumes of ice cold PBS and centrifuged again. The supernatant was discarded and cells were resuspended with an equal volume of PBS. Denaturing solution (0.36 ml of 2-mercaptoethanol/50 ml of guanidinium stock solution-4M guanidinium thiocyanate, 25 mM sodium citrate, pH 7.0, 0.5% sarkosyl) 10 ml per 1 g of cell pellet was added prior to use and mixed gently. Sodium acetate (pH 4.0, 1 ml of 2M), 10 ml of phenol saturated water and 2 ml of chloroform: isoamyl alcohol (24:1) mixtures were sequentially added after each addition. The solution was mixed thoroughly by inversion. The solution was vigorously shaken for 10 sec, chilled on ice for 15 min and then centrifuged 12,000×g for 30 min. The supernatant was transferred and an equal volume of 2-propanol was added and placed at −20° C. overnight to precipitate the RNA. The RNA was pelleted for 15 min at 12,000×g, and the pellet was resuspended with 2-3 ml of denaturing solution and 2 volumes of ethanol. The solution was placed at −20° C. for 2 h, and then centrifuged at 12,000×g for 15 min. The RNA pellet was washed with 70% ethanol and then 100% ethanol. The pellet was resuspended with RNase-free water (DEPC-treated water) after centrifugation at 12,000×g for 5 min. The amount of isolated RNA was measured spectrophotometrically and calculated from the absorbance at 280 nm and 260 nm.

The poly(A)mRNA isolation kit was purchased from Stratagene. Total RNA was applied to an oligo(dT) cellulose column after heating the total RNA at 65° C. for 5 min. Before applying, the RNA samples were mixed with 500 µl of 10× sample buffer (10 mM Tris-HCl, pH 7.5, 1 mM EDTA, 5 M NaCl). The RNA samples were pushed through the column at a rate of 1 drop every 2 sec. The eluates were pooled and reapplied to the column and purified again. Preheated elution buffer (65° C.) was applied, and mRNA was eluted and collected in 1.5 ml of centrifuge tubes on ice. The amount of mRNA was determined at OD260 (1 OD unit=40 µg of RNA). The amounts of total RNA and mRNA obtained from $4 \times 10^8$ cells were 1328 µg and 28 µg, respectively.

mRNA (1-2 µg) dissolved in DEPC-treated water was used for cDNA synthesis. mRNA isolated on three different dates was pooled for first-strand cDNA synthesis. The cDNA synthesis kit was purchased from Pharmacia Biotech. mRNA (1.5 µg/5 µl of DEPC-treated water) was heated at 65° C. for 10 min. and cooled immediately on ice. The primed first strand mix containing MuLV reverse transcriptase (11 µl) and appropriate buffers for the reaction were mixed with mRNA sample. DTT solution (1 µl of 0.1 M) and RNase-free water (16 µl) also were added to the solution. The mixture was incubated for 1 h at 37° C.

Degenerate primers for light chain and heavy chain (Novagen, Madison, Wis.) were used for PCR. PCR synthesis was carried out in 100 µl reaction volumes in 0.5 ml microcentrifuge tubes by using Robocycler (Stratagene, La Jolla, Calif.). All PCR syntheses included 2 µl of sense and anti-sense primers (20 pmoles/µl), 1 µl of first-strand cDNA as a template, 2 µl of 10 mM of dNTPs, 1 µl of Vent polymerase (2 units/µl), 10 µl of 10×PCR buffer (100 mM Tris-HCl, pH 8.8 at 25° C., 500 mM KCl, 15 mM MgCl2, 1% Triton X-100), 82 µl of H2O. Triton X-100 is t-octylphenoxypolyethoxyethanol. All PCR profiles consisted of 1 min of denaturation at 94° C., 1 min of annealing at 55° C., and 1 min of extension at 72° C. This sequence was repeated 30 times with a 6-min extension at 72° C. in the final cycle. PCR products were purified with QIAEX II gel extraction kit from Qiagen, Valencia, Calif. PCR amplification products for heavy and light chain coding sequences were analyzed by agarose gel electrophoresis and were about 340 base pair (bp) long and 325 bp long, respectively.

Total RNA or DNA was analyzed by agarose gel electrophoresis (1% agarose gels). Agarose (0.5 g in 50 ml of TAE buffer, 40 mM Tris-acetate, 1 mM EDTA) was heated for 2 min in a microwave to melt and evenly disperse the agarose. The solution was cooled at room temperature, and ethidium bromide (0.5 µg/ml) was added and poured into the apparatus. Each sample was mixed with 6× gel loading buffer (0.25% bromophenol blue, 0.25% xylene cyanol FF, 40% (w/v) sucrose in water). TAE buffer was used as the running buffer. Voltage (10 v/cm) was applied for 60-90 min.

According to the proper size for heavy and light chain cDNAs, the bands were excised from the gels under UV illumination, and excised gels were placed in 1 ml syringes fitted with 18-gauge needles. Gels were crushed to a 1.5 ml Eppendorf tube. The barrel of each syringe was washed with 200 µl of buffer-saturated phenol (pH 7.9+/−0.2). The mixture was thoroughly centrifuged and frozen at −70° C. for 10 min. The mixture was centrifuged for 5 min, and the top aqueous phase was transferred to a new tube. The aqueous phase was extracted again with phenol/chloroform (1:1). After centrifuging for 5 min, the top aqueous phase was transferred to a clean tube, and chloroform extraction was performed. Sodium acetate (10 volumes of 3 M) and 2.5 volumes of ice-cold ethanol were added to the top aqueous phase to precipitate DNA at −20° C. overnight.

Purified heavy and light chain cDNAs were ligated into plasmid pSTBlue-1 vector and transfected into NovaBlue competent cells (Stratagene). Colonies containing heavy and light chain DNAs were screened by blue and white colony selection and confirmed by PCR analysis. Heavy and light chain DNAs were isolated and sequenced using standard techniques. Tables 2A and 2B show the DNA sequences of heavy and light chain DNAs of ScFv. See also SEQ ID NO: 3 and SEQ ID NO: 4.

PCR amplification and the assembly of single ScFv gene was according to Davis et al. (1991) Bio/Technology 9:165-169. Plasmid pSTBlue-1 carrying VH and VL genes were combined with all four oligonucleotide primers in a single PCR synthesis. Following first PCR synthesis, one tenth of the first PCR product was removed and added to a second PCR reaction mixture containing only the primer a (VH sense primer) and primer d (VL Antisense primer). The product of the second PCR synthesis yielded single ScFv gene. The single ScFv gene was ligated to plasmid pT-Adv (Clontech, Palo Alto, Calif.). pT-Adv carrying ScFv gene was used for DNA sequencing.

The complete ScFv gene was assembled from the VH, VL and linker genes to yield a single ScFv gene by PCR (Tables 2A and 2B). The DNA sequence encoding the linker was 45 nucleotides long (GGAGGCGGTGGATCGGGCGGTG-GCGGCTCGGGTGGCGGCGGCTCT; SEQ ID NO:6), which translates to a peptide of 15 amino acids (GlyGlyG-lyGlySerGlyGlyGlyGlySerGlyGlyGlyGlySer; SEQ ID NO:5). Primers for PCR amplification are shown in Tables 2A and 2B. S-peptide was linked to the C-terminus of ScFv[ScFv(S)]. S-peptide binds to S-protein conjugated to alkaline phosphatase for Western blot analysis. The DNA sequence of the S-peptide is AAAGAAACCGCTGCT-GCTAAATTCGAACGCCAGCACATGGACAGC (SEQ ID NO:7) which translates to S-peptide (LysGluThrAl-aAlaAlaLysPheGluArgGln HisMetAspSer; SEQ ID NO:8).

Recombinant ScFv(S) was expressed in *E. coli*. First, oligo nucleotides encoding S-peptide were linked to the 3' end of the open reading frame (ORF) of ScFv DNA by PCR amplification. Incorporation of S-peptide enables to detect expressed ScFv protein by S-protein conjugated to alkaline phosphatase. The ENOX2-specific ScFv(S) coding sequence was then subcloned to plasmid pET-11a, a plasmid designed for protein expression in *E. coli* (Stratagene, CA). For PCR amplification, two primers were designed to amplify ORF of ScFv(S) containing endonuclease restriction sites (NdeI and NheI) and S-peptide residues.

Plasmid pET-11a and ORF of ScFv(S) were digested with restriction enzymes NdeI and NheI and ligated to produce plasmid pET11-ScFv(S). *E. coli* BL21 (DE3) was transformed with pET11-ScFv(S) and grown at 37° C. for 12 h in LB medium containing ampicillin (100 μg/ml). ScFv was expressed by addition of 0.5 mM IPTG and incubation for 4 h. Cells were harvested and lysed using a French Pressure Cell (French Pressure Cell Press, SLM Instruments, Inc.) (three passages at 20,000 psi). Cell extracts were centrifuged at 10,000×g for 20 min. Pellets containing denatured inclusion bodies of ScFv were collected. Renaturation of the inclusion bodies of the ScFv was according to Goldberg et al. (1995) Folding & Design 1:21-27.

TABLE 1A

DNA Sequence of Heavy chain ScFv ($V_H$), SEQ. ID NO: 1

```
  1  gaggtcaagc tgcaggagtc aggaactgaa gtggtaaagc
     ctggggcttc
 51  agtgaagttg tcctgcaagg cttctggcta catcttcaca
     agttatgata
101  tagactgggt gaggcagacg cctgaacagg gacttgagtg
     gattggatgg
151  attttcctg gagaggggag tactgaatac aatgagaagt
     tcaagggcag
201  ggccacactg agtgtagaca agtcctccag cacagcctat
     atggagctca
251  ctaggctgac atctgaggac tctgctgtct atttctgtgc
     tagagggac
301  tactataggc gctactttga cttgtgggc caagggacca
     cggtcaccgt
351  ctcctca
```

TABLE 1B

DNA Sequence of Light chain ScFv ($V_L$), SEQ. ID NO: 2

```
  1  gaaaatgtgc tcacccagtc tccagcaatc atgtctgcat
     ctccagggga
 51  gagggtcacc atgacctgca gtgccagctc aagtatacgt
     tacatatatt
101  ggtaccaaca gaagcctgga tcctccccca gactcctgat
     ttatgacaca
151  tccaacgtgg ctcctggagt ccctttcgc ttcagtggca
     gtgggtctgg
201  gacctcttat tctctcacaa tcaaccgaat ggaggctgag
     gatgctgcca
251  cttattactg ccaggagtgg agtggttatc cgtacacgtt
     cggaggggg
301  accaagctgg agctgaaagc g
```

TABLE 2A

DNA Sequence for ScFv, SEQ. ID NO: 3

```
  1  gtggtaaagc ctggggcttc
 51  gaggtcaagc tgcaggagtc aggaactgaa catcttcaca
     agttatgata
101  agtgaagttg tcctgcaagg cttctggcta gacttgagtg
     gattggatgg
151  tagactgggt gaggcagacg cctgaacagg aatgagaagt
     tcaagggcag
201  ggccacactg agtgtagaca agtcctccag cacagcctat
     atggagctca
251  ctaggctgac atctgaggac tctgctgtct atttctgtgc
     tagagggac
301  tactataggc gctactttga cttgtgggc caagggacca
     cggtcaccgt
```

TABLE 2A-continued

DNA Sequence for ScFv, SEQ. ID NO: 3

```
351  ctcctcagga ggcggtggat cgggcggtgg cggctcggt
     ggcggcggct 401  ctgaaaatgt gctcacccag tctccagcaa tcatgtctgc
     atctccaggg 451  gagagggtca ccatgacctg cagtgccagc tcaagtatac
     gttacatata 501  ttggtaccaa cagaagcctg gatcctcccc cagactcctg
     atttatgaca 551  catccaacgt ggctcctgga gtcccttttc gcttcagtgg
     cagtgggtct 601  gggacctctt attctctcac aatcaaccga atggaggctg
     aggatgctgc 651  cacttattac tgccaggagt ggagtggtta tccgtacacg
     ttcggagggg 701  ggaccaagct ggagctgaaa gcgaaagaaa ccgctgctgc
     taaattcgaa 751  cgccagcaca tggacagc  s-peptide
```

TABLE 2B

Amino Acid Sequence for ScFv, SEQ. ID NO: 4

```
  1  EVKLQESGTE VVKPGASVKL SCKASGYIFT SYDIDWVRQT
     PEQGLEWIGW

51  IFPGEGSTEY NEKFKGRATL SVDKSSSTAY MELTRLTSED
     SAVYFCARGD

101  YYRRYFDLWG QGTTVTVSSG GGGSGGGGSG GGGSENVLTQ
     SPAIMSASPG

151  ERVTMTCSAS SSIRYIYWYQ QKPGSSPRLL IYDTSNVAPG
     VPFRFSGSGS

201  GTSYSLTINR MEAEDAATYY CQEWSGYPYT FGGGTKLELK
     AKETAAAKFE

251  RQHMDS  s-peptide
```

TABLE 3

Primers for PCR amplification of scFv(s) gene

1. Primers for cloning of variable regions of heavy chain and light chain of antibody
(A) Primers for heavy chain (vH)
Forward primer: 5'-GGCCCAGCCGGCCGAGGTCAAGCTGCAGGAG TCAGGA-3' (SEQ ID NO: 9)
Reverse primer: 5'-CTCGGAACCTGAGGAGACGGTGACCGTGGT CCC-3' (SEQ ID NO: 10)

(B) Primers for light chain (VL)
Forward primer: 5'-TCCAAAGTCGACGAAAATGTGCTCACCCAGT CTCCA-3' (SEQ ID NO: 11)
Reverse primer: 5'-AGCGGCCGCTTTCAGCTCCAGCTTGGTCCCC CC-3' (SEQ ID NO: 12)

2. Primers for subcloning of ScFv(s) gene into pET-11a expression vector
(A) Primers for heavy chain (VH) and linker amplification
Forward primer: 5'-GTCAAGCTGCAGGAGTCAGGA-3' (SEQ ID NO: 13)

TABLE 3-continued

Primers for PCR amplification of scFv(s) gene

Reverse primer: 5'-AGAGCCGCCGCCACCCGAGCCGCCACCGCCC GATCCACCGCCTCCTGAGGAGACGGTGACCGTGGT-3' (SEQ ID NO: 14)

(B) Primers for light chain (VL), linker and S-tag amplification
Forward primer: 5'-GGAGGCGGTGGATCGGGCGGTGGCGGCTCGG GTGGCGGCGGCTCTGAAAATGTGCTCACCCAGTCT-3' (SEQ ID NO: 15)
Reverse primer: 5'-AGTCAGGCTAGCTTAGCTGTCCATGTGCTGG CGTTCGAATTTAGCAGCAGCGGTTTCTTTCGCTTTCAGCTCCAGCTT-3' (SEQ ID NO: 16)

Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) Molecular Cloning, Second Edition, Cold Spring Harbor Laboratory, Plainview, N.Y.; Maniatis et al. (1982) Molecular Cloning, Cold Spring Harbor Laboratory, Plainview, N.Y.; Wu (ed.) (1993) Meth. Enzymol. 218, Part I; Wu (ed.) (1979) Meth. Enzymol. 68; Wu et al. (eds.) (1983) Meth. Enzymol. 100 and 101; Grossman and Moldave (eds.) Meth. Enzymol. 65; Miller (ed.) (1972) Experiments in Molecular Genetics, Cold Spring Harbor Laboratory, Cold Spring Harbor, N.Y.; Old and Primrose (1981) Principles of Gene Manipulation, University of California Press, Berkeley; Schleif and Wensink (1982) Practical Methods in Molecular Biology; Glover (ed.) (1985) DNA Cloning Vol. I and II, IRL Press, Oxford, UK; Hames and Higgins (eds.) (1985) Nucleic Acid Hybridization, IRL Press, Oxford, UK; Setlow and Hollaender (1979) Genetic Engineering: Principles and Methods, Vols. 1-4, Plenum Press, New York; Fitchen, et al. (1993) Annu Rev. Microbiol. 47:739-764; Tolstoshev, et al. (1993) in Genomic Research in Molecular Medicine and Virology, Academic Press; and Ausubel et al. (1992) Current Protocols in Molecular Biology, Greene/Wiley, New York, N.Y. Abbreviations and nomenclature, where employed, are deemed standard in the field and commonly used in professional journals such as those cited herein. Antibody vaccines are described in Dillman R. O. (2001) Cancer Invest. 19(8):833-841. Durrant L. G. et al. (2001) Int J. Cancer 1; 92(3):414-20 and Bhattacharya-Chatterjee M, (2001) Curr. Opin. Mol. Ther. February; 3(1):63-9 describe anti-idiotype antibodies. Many of the procedures useful for practicing the present invention, whether or not described herein in detail, are well known to those skilled in the arts of molecular biology, biochemistry, immunology, and medicine.

Monoclonal, polyclonal antibodies, peptide-specific antibodies or single chain recombinant antibodies and antigen binding fragments of any of the foregoing, specifically reacting with the ENOX2 isoform proteins described herein, may be made by methods known in the art. See e.g., Harlow and Lane (1988) Antibodies: A Laboratory Manual, Cold Spring Harbor Laboratories; and Goding (1986) Monoclonal Antibodies: Principles and Practice, 2d ed., Academic Press, New York.

All references cited in the present application are incorporated by reference herein to the extent that there is no inconsistency with the present disclosure. Such references reflect the skill in the arts relevant to the present invention.

The examples provided herein are for illustrative purposes, and are not intended to limit the scope of the invention as claimed herein. Any variations in the exemplified antibodies, epitopes, purification methods, diagnostic methods, preventative methods, treatment methods, and other methods which occur to the skilled artisan are intended to fall within the scope of the present invention.

What is claimed is:

1. A method for detecting the presence of one or more ENOX2 transcript variants comprising:
   obtaining a sample suspected of having one or more ENOX2 transcript variants;
   electrophoretically separating the one or more ENOX2 transcript variants; and
   determining the presence of the one or more ENOX2 transcript variants using a single chain variable region ENOX2 antibody linked directly to alkaline phosphatase or other single step agent for detection or imaging.

2. The method of claim 1, further comprising the step of detecting a benign to malignant transformation in the sample at least 5 years before clinical symptoms by detecting the emergence of one or more tissue-specific ENOX2 transcript variants in the sample.

3. The method of claim 1, wherein the single chain variable region ENOX2 antibody is conjugated directly to a detectable marker.

4. The method of claim 1, wherein the single chain variable region ENOX2 antibody has SEQ ID NO:4.

5. The method of claim 1, further comprising the step of separating the one or more ENOX2 transcript variants electrophoretically on a two-dimensional gel that separates based on molecular weight and isoelectric point, wherein the presence of one or more ENOX2 transcript variants at specific molecular weights and isoelectric points is indicative of malignant transformation of the cells in the sample.

6. The method of claim 1, wherein the sample is a blood, serum, or plasma sample.

7. The method of claim 1, further comprising the step of determining the presence of a benign to malignant cell transformation and a cell type or tissue of cancer origin for the malignant cells.

8. The method of claim 1, further comprising the step of determining a cell type or tissue of cancer origin for a sample previously identified as a cancer of unknown origin.

9. The method of claim 1, further comprising the step of determining a cell type or tissue of cancer origin for a sample previously identified as a cancer of unknown origin as being selected from cervical, ovarian, prostate, breast/uterine, non-small cell lung, small cell lung, pancreatic, colon, lymphoma/leukemia or melanoma.

10. An assay for detecting the presence of one or more ENOX2 transcript variant comprising:
    obtaining a sample suspected of having one or more ENOX2 transcript variants;
    electrophoretically separating the one or more ENOX2 transcript variants;
    measuring the presence of the one or more ENOX2 transcript variants in the sample using a single chain variable region ENOX2 antibody linked directly to alkaline phosphatase or other single step agent for detection or imaging; and
    detecting a benign to malignant transformation in the sample at least 5 years before clinical symptoms by detecting the emergence of one or more tissue-specific ENOX2 transcript variants in the sample.

11. The method of claim 10, wherein the sample is a blood, serum, or plasma sample.

12. The method of claim 10, further comprising the step of determining the presence of a benign to malignant cell transformation and a cell type or tissue of cancer origin for the malignant cells.

13. The method of claim 10, further comprising the step of determining a cell type or tissue of cancer origin for a sample previously identified as a cancer of unknown origin.

14. The method of claim 10, further comprising the step of determining a cell type or tissue of cancer origin for a sample previously identified as a cancer of unknown origin as being selected from cervical, ovarian, prostate, breast/uterine, non-small cell lung, small cell lung, pancreatic, colon, lymphoma/leukemia or melanoma.

15. A method for detecting the presence of one or more ENOX2 transcript variants to determine the cell or tissue of origin of a malignant cancer previously identified an being a cancer of unknown origin comprising:
   obtaining a sample suspected of having one or more ENOX2 transcript variants;
   electrophoretically separating the one or more ENOX2 transcript variants;
   detecting the presence of the one or more ENOX2 transcript variants using a single chain variable region ENOX2 antibody linked directly to an alkaline phosphatase or other single step agent for detection or imaging; and
   determining the actual origin or origins of the cancer of unknown origin, wherein the cancer is now identified as being a cancer of cervical, ovarian, prostate, breast/uterine, non-small cell lung, small cell lung, pancreatic, colon, lymphoma/leukemia or melanoma based on the molecular weight and isoelectric point of the one or more ENOX2 transcript variants, wherein the actual origin or origins of the cancer are determined at least 5 years before clinical symptoms by detecting the emergence of one or more tissue-specific ENOX2 transcript variants in the sample.

16. The method of claim 15, wherein the sample is a blood, serum, or plasma sample.

17. The method of claim 15, wherein the single chain variable region ENOX2 antibody is conjugated directly to a detectable marker.

18. The method of claim 15, wherein the single chain variable region ENOX2 antibody has SEQ ID NO:4.

19. The method of claim 15, further comprising the step of separating the one or more ENOX2 transcript variants electrophoretically on a two-dimensional gel that separates based on molecular weight and isoelectric point, wherein the presence of one or more ENOX2 transcript variants at specific molecular weights and isoelectric points is indicative of malignant transformation of the cells in the sample.

20. The method of claim 15, further comprising the step of determining the presence of a benign to malignant cell transformation and a cell type or tissue of cancer origin for the malignant cells.

\* \* \* \* \*